United States Patent [19]
Gilmore et al.

[11] Patent Number: 5,281,593
[45] Date of Patent: Jan. 25, 1994

[54] CERTAIN INDOLE DERIVATIVES USEFUL AS LEUKOTRIENE ANTAGONISTS

[75] Inventors: Jeremy Gilmore, Paddock Hill Frimley; Alec Todd, Wokingham, both of United Kingdom

[73] Assignee: Lilly Industries Limited, Basingstoke, England

[21] Appl. No.: 54,914

[22] Filed: Apr. 29, 1993

Related U.S. Application Data

[63] Continuation of Ser. No. 984,013, Nov. 30, 1992, abandoned, which is a continuation of Ser. No. 917,529, Jul. 17, 1992, abandoned, which is a continuation of Ser. No. 736,176, Jul. 26, 1991, abandoned.

[30] Foreign Application Priority Data

Jul. 31, 1990 [GB] United Kingdom ............... 9016790
Apr. 9, 1991 [GB] United Kingdom ............... 9107486

[51] Int. Cl.$^5$ .................. A61K 31/47; C07D 401/10; C07D 401/12
[52] U.S. Cl. .................. 514/249; 514/259; 514/314; 514/339; 514/365; 514/367; 514/374; 544/284; 544/353; 546/174; 546/175; 546/176; 546/177; 546/273; 548/159; 548/181; 548/217
[58] Field of Search ............... 544/284, 353; 546/174, 546/175, 176, 177, 273; 548/159, 181, 217; 514/249, 259, 314, 339, 365, 367, 374

[56] References Cited

U.S. PATENT DOCUMENTS 4,555,569 11/1985 Zink et al. ..................... 544/284

FOREIGN PATENT DOCUMENTS 0179619 4/1986 European Pat. Off.
0242167 10/1987 European Pat. Off.
0290145 11/1988 European Pat. Off.
WO89/05294 6/1989 PCT Int'l Appl.

OTHER PUBLICATIONS

Youssefyeh et al., *J. Med. Chem.*, 33, 1186–1194 (1990).
Hyany et al., *J. Med. Chem.*, 33, 1194–1200 (1990).
Yee et al., *J. Med. Chem.*, 33, 2437–2451 (1990).

Primary Examiner—C. Warren Ivy
Assistant Examiner—James H. Turnipseed
Attorney, Agent, or Firm—Roger S. Benjamin; Leroy Whitaker; John C. Demeter

[57] ABSTRACT

A compound of the formula

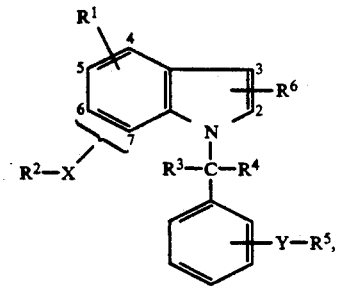

in which $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehydo, $-CH_2Z$, $-CH=CH-Z$ or $-CH_2CH_2Z$ where Z is optionally protected carboxy or optionally protected tetrazolyl; $R^2$ is halo, nitrile, an optionally protected acid group or $-CONR^7R^8$ where $R^7$ and $R^8$ are each hydrogen or $C_{1-4}$ alkyl; $R^3$ and $R^4$ are each hydrogen, $C_{1-4}$ alkyl, optionally substituted phenyl, or $C_{1-4}$ alkyl substituted by $-CONR^7R^8$ or an optionally protected acid group; $R^5$ is

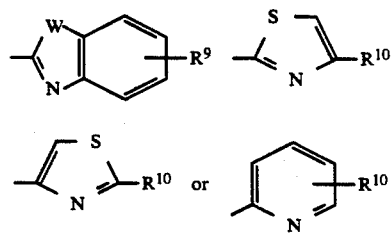

where W is $-CH=CH-$, $-CH=N-$, $-N=CH-$, $-O-$ or $-S-$, $R^9$ is hydrogen, halo, $C_{1-4}$ alkyl, $C_{1-4}$ (Abstract continued on next page.)

ABSTRACT
*-continued* alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl; X is $-O-(CH_2)_n CR^{11}R^{12}$, $-CR^{11}R^{12}-$, $-CR^{11}R^{12}.(CH_2)_n.CR^{13}R^{14}-$ or $-CR^{11}=CR^{12}-$ where $R^{11}$, $R^{12}$, $R^{13}$ and $R^{14}$ are each hydrogen or $C_{1-4}$ alkyl, and n is 0, 1 or 2; and Y is $-O-CR^{15}R^{16}-$, $-CR^{15}=CR^{16}-$ or $-CR^{15}R^{16}.CR^{17}R^{18}-$ where $R^{15}$, $R^{16}$, $R^{17}$ and $R^{18}$ are each hydrogen or $C_{1-4}$ alkyl; or a salt thereof. The compounds in unprotected form are active as leukotriene antagonists.

61 Claims, No Drawings

CERTAIN INDOLE DERIVATIVES USEFUL AS LEUKOTRIENE ANTAGONISTS

This application is a continuation of application Ser. No. 07/984,013, filed on Nov. 30, 1992; which is a continuation of application Ser. No. 07/917,529 filed on Jul. 17, 1992; which is continuation of application Ser. No. 07/736,176 filed on Jul. 26, 1991 all now abandoned.

This invention relates to pharmaceutical compounds, their use and preparation.

The compounds of the invention are of the formula

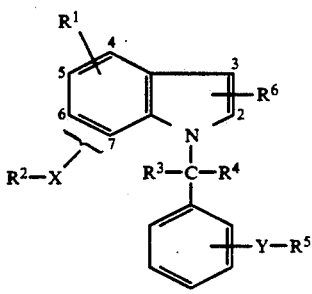

I

The compounds of the invention are of the formula in which $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehydo, —$CH_2Z$, —CH=CH—Z or —$CH_2CH_2Z$ where Z is optionally protected carboxy or optionally protected tetrazolyl; $R^2$ is halo, nitrile, an optionally protected acid group or —$CONR^7R^8$ where $R^7$ and $R^8$ are each hydrogen or $C_{1-4}$ alkyl; $R^3$ and $R^4$ are each hydrogen, $C_{1-4}$ alkyl, optionally substituted phenyl, or $C_{1-4}$ alkyl substituted by —$CONR^7R^8$ or an optionally protected acid group; $R^5$ is

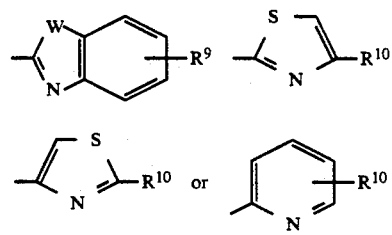

where W is —CH=CH—, —CH=N—, —N=CH—, —O— or —S—, $R^9$ is hydrogen, halo, $C_{1-4}$ alkyl, $C_{1-4}$ alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl; X is —O—$(CH_2)_n$$CR^{11}R^{12}$, —$CR^{11}R^{12}$—, —$CR^{11}R^{12}.(CH_2)_n.CR^{13}R^{14}$— or —$CR^{11}$=$CR^{12}$— where $R^{11}, R^{12}, R^{13}$ and $R^{14}$ are each hydrogen or $C_{1-4}$ alkyl, and n is 0, 1 or 2; and Y is —O—$CR^{15}R^{16}$—, —$CR^{15}$=$CR^{16}$— or —$CR^{15}R^{16}.CR^{17}R^{18}$— where $R^{15}$, $R^{16}$, $R^{17}$ and $R^{18}$ are each hydrogen or $C_{1-4}$ alkyl; and salts thereof.

The compounds of the invention are leukotriene antagonists. Thus the invention comprises compounds of Formula (I) in unprotected form, and their pharmaceutically-acceptable salts, for use in the treatment of diseases in which leukotrienes are a causal mediator.

In the above formula (I), a halo substituent can be for example, chloro, bromo and fluoro and is preferably chloro. A $C_{1-4}$ alkyl group includes methyl, ethyl, propyl, isopropyl, butyl and tert.butyl and is preferably methyl or ethyl, and a $C_{1-4}$ alkoxy group is one such alkyl group attached through oxygen. A hydroxy-$C_{1-4}$ alkyl group is a hydroxy-substituted $C_{1-4}$ alkyl group preferably of the formula $HO(CH_2)_n$— where n is 1 to 4, a preferred example being hydroxymethyl. A $C_{3-6}$ cycloalkyl group includes for example cyclopropyl, cyclopentyl and cyclohexyl, and is preferably cyclopropyl. The $C_{3-6}$ cycloalkyl group can be substituted by a $C_{1-4}$ alkyl. A $C_{2-6}$ alkenyl group is preferably propenyl or isopropenyl. A trihalomethyl group is preferably trifluoromethyl. An optionally substituted phenyl group is phenyl itself, or phenyl substituted with one or more, preferably 1 to 3, substituents selected from $C_{1-4}$ alkyl, especially methyl, $C_{1-4}$ alkoxy, especially methoxy and ethoxy, hydroxy, nitro, cyano, halo, especially chloro or fluoro, trihalomethyl, especially trifluoromethyl, carboxy, $C_{1-4}$ alkoxy-carbonyl, and optionally protected tetrazolyl.

An acid group can be any acid group conventionally used in pharmaceutical chemistry and the term includes, for example, tetrazolyl (1H-tetrazol-5-yl), carboxy (—COOH), phosphonate (—$PO(OH)_2$), sulphonate (—$SO_2OH$), acyl sulphonamido (—$CONHSO_2R$, where R is preferably $C_{1-4}$ alkyl or optionally substituted phenyl) or cyanoguanidinyl (—$NHC(NH_2)$=NCN). Especially preferred examples are tetrazolyl and carboxy.

When $R^5$ is the group

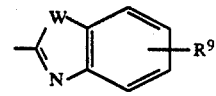

it comprises groups of the following type

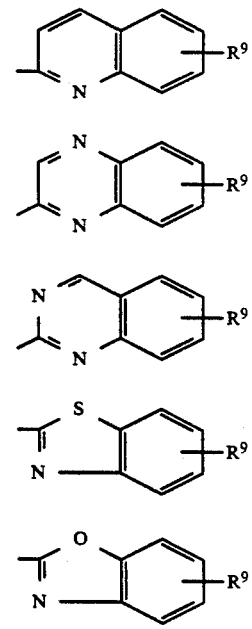

and the quinolin-2-yl group is the most preferred.

The value of $R^1$ is preferably hydrogen or halogen, and especially hydrogen, and when it is other than hydrogen it is preferably attached to the indole nucleus at the 4-position.

The group R²—X— is attached to the indole nucleus at the 6- or 7- position, and when X is —O—(CH₂)ₙCR¹¹R¹² via the oxygen atom. R² is preferably an acid group especially tetrazolyl or carboxy.

The groups R³ and R⁴ can be hydrogen, C₁₋₄ alkyl or optionally substituted phenyl, and preferred instances are those in which R³ and R⁴ are both hydrogen, R³ is hydrogen and R⁴ is C₁₋₄ alkyl or optionally substituted phenyl, and R³ and R⁴ are each C₁₋₄ alkyl, preferably methyl or ethyl. A further preferred instance is one in which R³ is C₁₋₄ alkyl substituted by an acid group and R⁴ is hydrogen or C₁₋₄ alkyl.

The R⁵ group is preferably quinolin-2-yl where the substituent R⁹, which is preferably hydrogen or halo, is attached at the 7-position. The group R⁵—Y— can be attached at the 2-, 3-or 4- positions to the phenyl nucleus, and when Y is —O—CR¹⁵R¹⁶— via the oxygen atom. R⁵—Y— is preferably attached at the 3-position.

The R⁶ group is preferably hydrogen and when it is C₁₋₄ alkyl is preferably attached at the 3-position.

The linking group X is preferably —O—CR¹¹R¹²— or CR¹¹R¹².CR¹³R¹⁴—, and R¹¹, R¹², R¹³ and R¹⁴ are preferably hydrogen. Linking group Y is preferably of the formula —O—CR¹⁵R¹⁶— or —CR¹⁵=CR¹⁶—, and R¹⁵, R¹⁶, R¹⁷ and R¹⁸ are preferably hydrogen.

When acid substituents on the compound of formula (I) require protection during preparation they may be protected by conventional protecting groups. Such protected compounds are included in the scope of the invention, though the preferred compounds with optimum biological properties are the unprotected compounds derived from them. A carboxy can be protected by protecting groups which include the well known ester forming groups used for the temporary protection of acidic carboxylic acid groups. Examples of such groups which have general use are readily hydrolysable groups such as arylmethyl groups, haloalkyl groups, trialkylsilyl groups, alkyl groups, and alkenyl groups. A preferred protected carboxy is C₁₋₄ alkoxy-carbonyl. Other carboxy protecting groups are described by E. Haslam in Protective Groups in Organic Chemistry. Such protecting groups are also suitable for protecting phosphonate and sulphonate substituents. Furthermore, it is usually necessary to protect any tetrazolyl group during the process of preparation, and suitable and well known protecting groups for this purpose include groups of the formula —CR'R''R''' where R' and R'' are hydrogen, C₁₋₄ alkyl or phenyl optionally substituted by one or more electron-donating group such as for example, C₁₋₄ alkoxy, and R''' is phenyl optionally substituted by one or more electron donating groups. Preferred examples include trityl and benzhydryl.

A particular group of compounds of the invention is of the formula

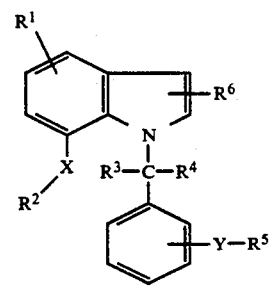

in which R¹ is hydrogen, halo, C₁₋₄ alkyl, C₁₋₄ alkoxy, nitrile, optionally protected carboxy, trihalomethyl, hydroxymethyl, aldehydo, —CH=CH—Z or —CH₂CH₂Z where Z is optionally protected carboxy; R² is optionally protected tetrazolyl, nitrile, optionally protected carboxy or —CONR⁷R⁸ where R⁷ and R⁸ are each hydrogen or C₁₋₄ alkyl; R³ and R⁴ are each hydrogen, C₁₋₄ alkyl or optionally substituted phenyl; R⁵ is

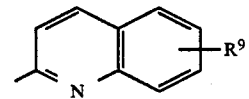

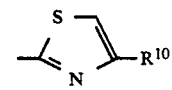

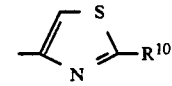

or

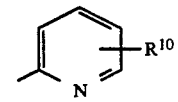

where R⁹ is hydrogen, halo, C₁₋₄ alkyl, C₁₋₄ alkoxy or trihalomethyl, and R¹⁰ is hydrogen, C₁₋₄ alkyl, C₂₋₆ alkenyl or C₃₋₆ cycloalkyl; R⁶ is hydrogen or C₁₋₄ alkyl; X is —O—CR¹¹R¹²—, —CR¹¹R¹²—, —CR¹¹R¹²(CH₂)ₙCR¹³R¹⁴— or —CR¹¹=CR¹²— where R¹¹, R¹², R¹³ and R¹⁴ are each hydrogen or C₁₋₄ alkyl, and n is 0, 1 or 2; and Y is —O—CR¹⁵R¹⁶—, —CR¹⁵=CR¹⁶— or —CR¹⁵R¹⁶CR¹⁷R¹⁸— where R¹⁵, R¹⁶, R¹⁷ and R¹⁸ are each hydrogen or C₁₋₄ alkyl; and salts thereof.

A further group of compounds of the invention is of the formula

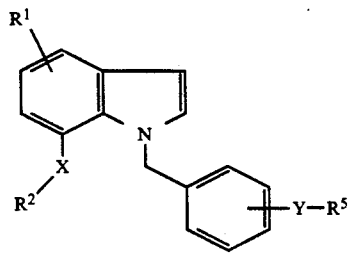

in which $R^1$ is hydrogen, halo, $C_{1-4}$ alkyl, $C_{1-4}$ alkoxy, nitrile, carboxy, $C_{1-4}$ alkoxy-carbonyl or trihalomethyl; $R^2$ is tetrazolyl, nitrile, carboxy, $C_{1-4}$ alkoxy-carbonyl or —$CONR^7R^8$ where $R^7$ and $R^8$ are each hydrogen or $C_{1-4}$ alkyl; $R^5$ is

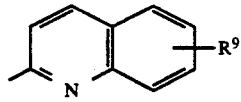

where $R^9$ is hydrogen, halo, $C_{1-4}$ alkyl, $C_{1-4}$ alkoxy or trihalomethyl; X is —O—$CR^{11}R^{12}$—, —$CR^{11}R^{12}$ $CR^{13}R^{14}$— or —$CR^{11}$=$CR^{12}$— where $R^{11}$, $R^{12}$, $R^{13}$ and $R^{14}$ are each hydrogen or $C_{1-4}$ alkyl; and Y is —O—$CR^{15}R^{16}$— or —$CR^{15}$=$CR^{16}$— where $R^{15}$ and $R^{16}$ are each hydrogen or $C_{1-4}$ alkyl; and salts thereof.

Preferred groups of compounds of the invention are (1) of the formula

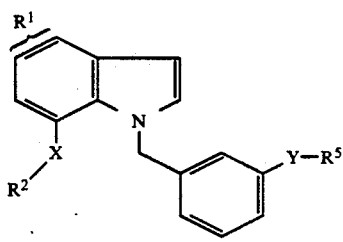

in which $R^1$ is hydrogen or halo, $R^2X$— is tetrazolyl—$CH_2O$— or tetrazolyl—$CH_2CH_2$—, and $R^5Y$— is

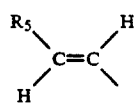

where $R^5$ is

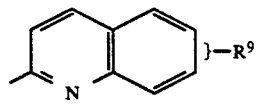

and $R^9$ is hydrogen or halo, and (2) of the formula

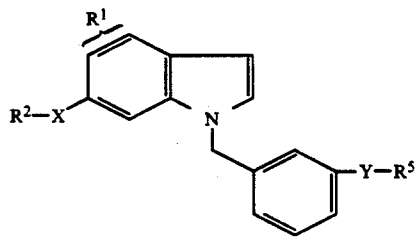

in which $R^1$ is hydrogen or halo, $R^2X$— is tetrazolyl—$CH_2$—, and $R^5Y$— is

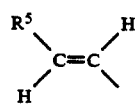

where $R^5$ is

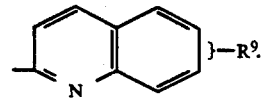

and $R^9$ is hydrogen or halo; the groups $R^1$ and $R^9$ being in the 4-or 5- positions and 6- or 7- positions, respectively.

It will be appreciated that the compounds of the invention can contain one or more asymmetric carbon atoms which gives rise to isomers. The compounds are normally prepared as racemic mixtures and can conveniently be used as such but individual isomers can be isolated by conventional techniques if so desired. Such racemic mixtures and individual optical isomers form part of the present invention and it is preferred to use an enantiomerically pure form. Compounds in which one or both of the linking groups is unsaturated yield geometric isomers, and for example when Y is unsaturated the trans compounds are preferred, being the more thermally stable.

It is, of course, possible to prepare salts of the compounds of the invention and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

The invention also includes a process for producing a compound of the formula (I) above, which comprises (1) reacting an indole of the formula with a compound of the formula

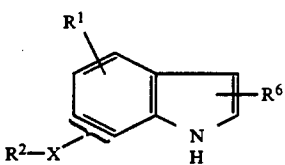

with a compound of the formula

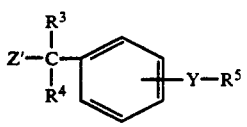

where Z' is a leaving group;
(2) reacting a compound of the formula

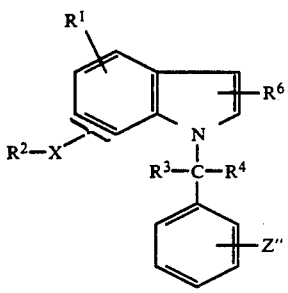

with a compound of the formula

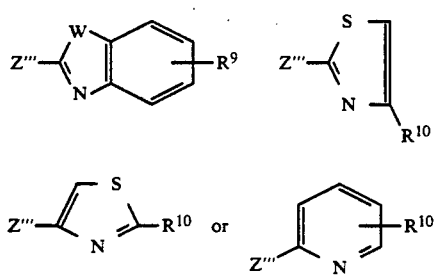

in which either Z" is —OH and Z'" is —CR$^{15}$R$^{16}$Z'
where Z' is a leaving group, or Z" is —CR$^{15}$=O
and Z'" is methyl or a Wittig-type moiety;
(3) alkylating a compound of the formula

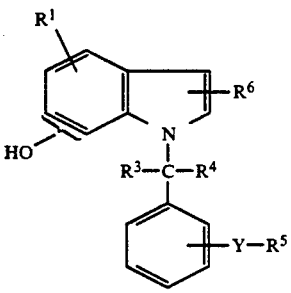

with a compound of formula R$^2$CR$^{11}$R$^{12}$(CH$_2$)$_n$Z'
where Z' is a leaving group, to give a compound of
formula (I) in which X is —O—(CH$_2$)$_n$CR$^{11}$R$^{12}$—;
(4) reacting a compound of the formula

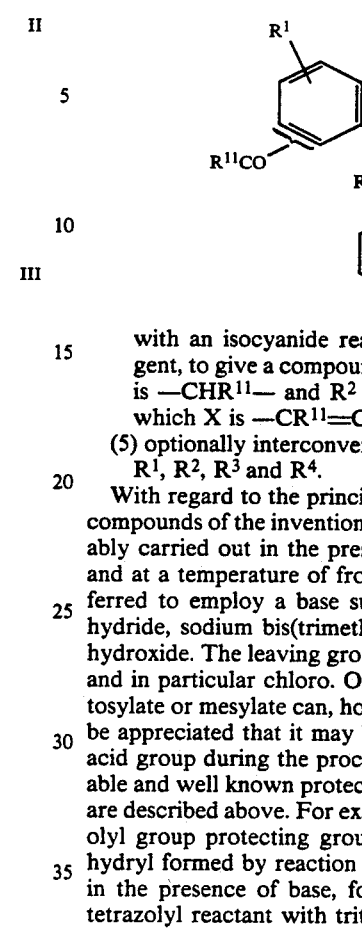

with an isocyanide reagent or a Wittig-type reagent, to give a compound of formula (I) in which X is —CHR$^{11}$— and R$^2$ is —CN or a compound in which X is —CR$^{11}$=CR$^{12}$—; or
(5) optionally interconverting one or more of groups R$^1$, R$^2$, R$^3$ and R$^4$.

With regard to the principal preparative route to the compounds of the invention (reaction (1)), this is preferably carried out in the presence of an organic solvent and at a temperature of from 0° C. to 50° C. It is preferred to employ a base such as for example sodium hydride, sodium bis(trimethylsilyl) azide or potassium hydroxide. The leaving group, Z', is preferably halogen and in particular chloro. Other leaving groups such as tosylate or mesylate can, however, be employed. It will be appreciated that it may be necessary to protect any acid group during the process of preparation, and suitable and well known protecting groups for this purpose are described above. For example in the case of a tetrazolyl group protecting groups include trityl and benzhydryl formed by reaction with the appropriate halide in the presence of base, for example by reacting the tetrazolyl reactant with trityl chloride and triethylamine. Other acid groups such as carboxy, phosphonate and sulphonate can be protected by the formation of esters in conventional manner.

Intermediate compounds of formula (II) can conveniently be prepared by the following main routes. Firstly, if it is desired to prepare the compound in which X is —O—(CH$_2$)$_n$CR$^{11}$R$^{12}$— attached via the oxygen to the 7- position on the phenyl nucleus, the starting point can be an appropriate ortho-nitrophenol which is first protected by for example benzylation, and reduced to give the aniline derivative. This can then be reacted with 2-methylthioacetaldehyde dimethyl acetal and the product cyclised by acid, as follows:

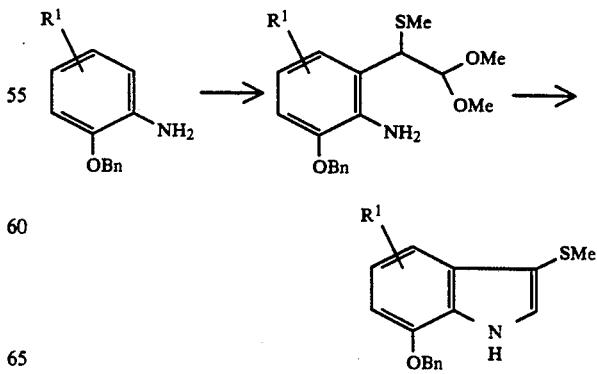

Removal of the methylthio substituent with Raney nickel and reduction with hydrogen and palladium gives an intermediate hydroxy-indole which, without necessarily being isolated, can be reacted in the presence of an appropriate base with suitable reagents of the formulae $Br(CH_2)_nCR^{11}R^{12}CN$ or $Br(CH_2)_nCR^{11}R^{12}CO_2R$, where R is $C_{1-4}$ alkyl, as follows:

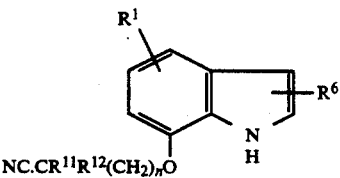
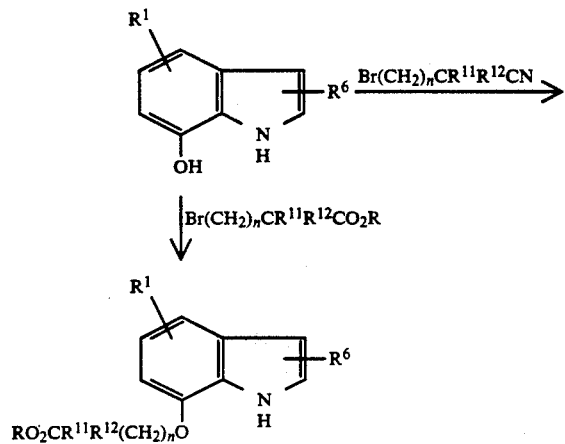

Compounds of formula (II) in which X is attached at the 7- position can, alternatively, be prepared from a compound of formula

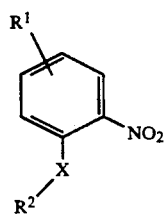

by reaction with three equivalents of vinyl Grignard reagent, or by a similar reaction on the protected ortho-nitro-phenol, protected benzaldehyde or benzoate, followed by alkylation or modification by Wittig reaction as described below.

If it is desired to prepare intermediates of formula (II) in which X is $-CR^{11}R^{12}-$, $-CR^{11}R^{12}(CH_2)_nCR^{13}R^{14}-$ or $-CR^{11}=CR^{12}-$, it is convenient to start from the appropriate 6- or 7-indole carboxylate:

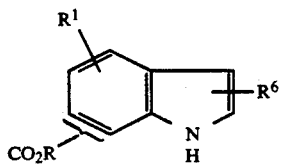

IV

The indole carboxylate can be reduced with, for example, lithium aluminium hydride, to the corresponding alcohol which in its turn can be oxidised to the aldehyde with a reagent such as pyridinium dichromate, as for example:

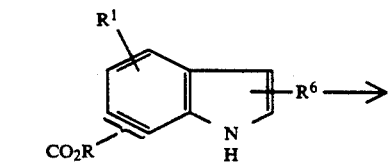

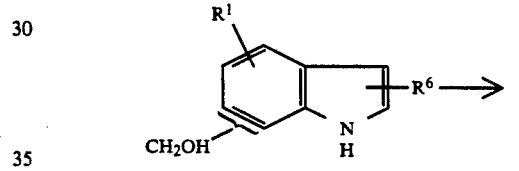

Alternatively, the 7-aldehyde can be synthesised by reaction of the bromo-nitrobenzene with alkenyl magnesium bromide and conversion of the bromo indole product by sodium hydride, t-butyl lithium and, for example, dimethylformamide to the aldehyde.

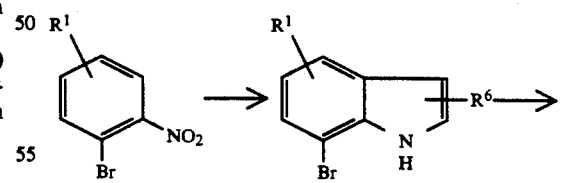

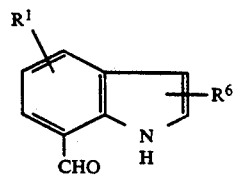

The aldehyde can then be reacted with, for example, dimethyl cyanomethyl phosphonate in the Wadsworth-Emmons reaction to give the corresponding unsaturated nitrile of formula (II) in which $-X-R^2$ is —CH=CHCN, reduction of which gives the compound in which —X—R² is —CH₂CH₂CN:

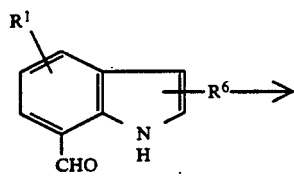

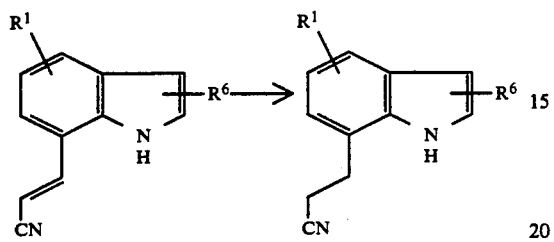

Compounds of formula (II) in which R² is protected tetrazolyl can be prepared by reacting the aldehyde with an optionally protected tetrazolylmethylphosphonate prepared, for example, by reacting the appropriate amide with PCl₅ and azide.

Compounds in which R¹¹, R¹², R¹³ and R¹⁴ are other than hydrogen can be made by suitable alteration of the above synthetic routes using conventional reaction methods.

The indole carboxylates of formula (IV) can be prepared by the Leimgruber and Batcho synthesis from the appropriate compound of formula

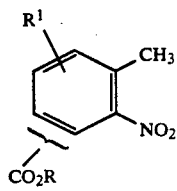

by reaction with dimethylformamide dimethyl acetal and cyclisation with catalytic reduction under hydrogen over palladium on charcoal. This reaction can also be utilised to prepare intermediates required for the synthesis of compounds of formula (II) in which X is —O—(CH₂)ₙCR¹¹R¹²— attached via the oxygen atom to the phenyl nucleus at the 6- position.

With regard to compounds of formula (III), these can be made by, for example, chlorination of the appropriate alcohol formed by coupling of the heterocyclic and benzene moieties, as for example, for quinolinyl derivatives:

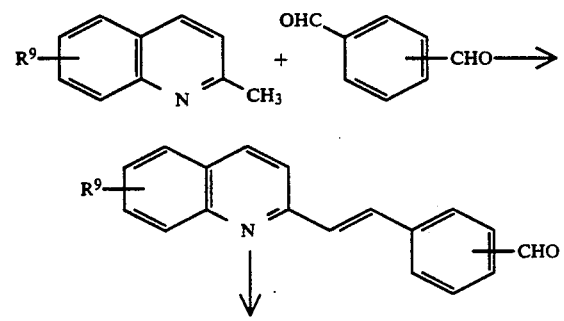

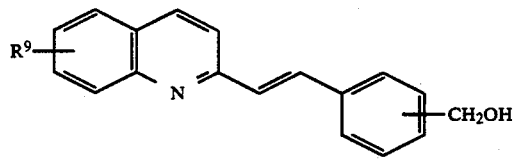

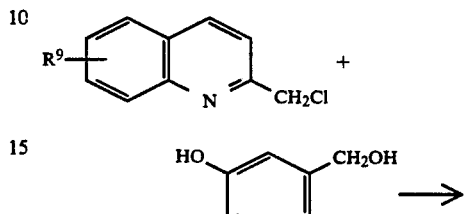

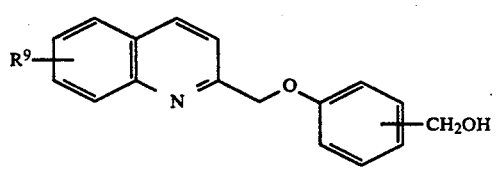

The alcohol intermediate in which R³ and/or R⁴ is other than hydrogen can be made by the reaction of Grignard reagents or alkyl or aryl lithiums on the above aldehydes, or acids or esters derived from them. In the case of compounds in which R³ or R⁴ is alkyl substituted by an acid group, the appropriate intermediate can be prepared by reaction with an acid substituted alkyl zincate. Standard methods can be employed to introduce values of R¹⁵, R¹⁶, R¹⁷ and R¹⁸ into the Y linking group between heterocycle R⁵ and phenyl nucleus.

An alternative route to the aldehyde reactants referred to above involves the use of an appropriate phosphonium ylid which can be reacted with phenyl dialdehyde to give the desired compound. This reaction can be employed to provide the thiazolyl and pyridyl reactants of formula (III).

The compounds of formula (I) above can be prepared by alternative routes to the condensation of compounds of formulae (II) and (III), as set out above in reaction steps (2), (3) and (4).

With regard to reaction (2), this is preferably carried out in an organic solvent and in the presence of base such as for example an alkali metal hydroxide or carbonate or an alkali metal hydride, in order to effect reaction between the compounds in which Z″ is —OH and Z‴ is —CR¹⁵R¹⁶Z′, preferably at a temperature of from 0° C. to 150° C. The aldehyde or ketone compound in which Z″ is

can be reacted with a compound in which Z‴ is methyl with acetic anhydride, optionally in an organic solvent such as for example xylene or toluene. When the reactant is of the type in which Z‴ is a moiety derived from an appropriate Wittig-type reagent, for example a Wittig or Wadsworth-Emmons reagent of the formula

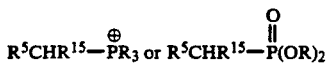

where R is an alkyl or aryl group, preferably $C_{1-4}$ alkyl or phenyl, the reaction is preferably carried out in an organic solvent in the presence of an appropriate base such as an alkali metal hydride or organo lithium compound, and at a temperature of, for example, from $-70°$ C. to 50° C.

With regard to reaction (3), this is carried out under conventional alkylation conditions, preferably at a temperature of from 0° C. to 120° C. and using an organic solvent such as for example methyl ethyl ketone, dimethylformamide, tetrahydrofuran or dimethoxyethane and in the presence of a base such as an alkali metal hydroxide or carbonate or an alkali metal hydride.

With regard to reaction (4), this involves reacting a ketone or aldehyde with an isocyanide reagent of the formula $Z'CHR^{12}.NC$ where $Z'$ is a leaving group, for example p-toluenesulphonylmethyl isocyanide. This reaction can be performed by reacting the isocyanide with a base such as potassium tert. butoxide in a solvent such as, for example, dimethoxyethane at a temperature of, for example, $-80°$ C. to 0° C. Alternatively, the same ketone or aldehyde compound can be reacted with an appropriate Wittig or Wadsworth-Emmons reagent of the formula

under the conditions outlined for reaction (2) above.

It will be appreciated that the product of reaction steps (1) to (4) can be further altered by variation of one or more $R^1$, $R^2$, $R^3$ or $R^4$ group. Thus, for example, it is possible to effect the following conversions:
 (i) removal of a protecting group from an acid group, such as a protected tetrazolyl or protected carboxy substituent, to give the free acid,
 (ii) conversion of a nitrile group to a tetrazolyl substituent,
 (iii) hydrolysis of a $C_{1-4}$ alkoxy-carbonyl group to carboxy,
 (iv) conversion of a carboxy or $C_{1-4}$ alkoxy-carbonyl group to an amido group $-CONR^7R^8$, or
 (v) alkylation of an amido group to provide other values of $-CONR^7R^8$.

A process for preparing a preferred group of compounds in which $R^2$ is tetrazolyl comprises removing the protecting group from a compound of formula (I) in which $R^2$ is protected tetrazolyl with, for example, acid. A further process for providing such compounds comprises reacting a compound of formula (I) in which $R^2$ is nitrile with a suitable azide, for example, tributyltin azide, optionally in an organic solvent such as for example dimethoxyethane, or an inorganic azide in dimethyl formamide, at a temperature of from 60° C. to 150° C. or 180° C., to provide a compound in which $R^2$ is tetrazolyl.

The compounds of the invention, excluding those in which the groups are in protected form and intermediate compounds in which $R^2$ is halo or nitrile, are pharmacologically active, being leukotriene antagonists as shown by the test of Fleisch et al. (J. Pharmacol. Exp.Ther., 233, 148-157) using the method described by Boot et al. (Br.J.Pharmacol. (1989), 98, 259-267).

Isolated guinea pig ileum was suspended in Tyrode solution at 37° C. and aerated with 95% oxygen and 5% carbon dioxide. Concentration response curves to leukotriene were generated and the effects of different concentration of drug investigated. Dissociation constants ($K_b$) of the receptor-inhibitor complex were calculated by the method of Furchgott (Furchgott R. F. Handbook of Experimented Pharmacology, New York, Vol. 33 pages 383-385). The title compounds disclosed in the following Examples have a $pK_b$ of 7 to 11.

The compounds were also active in the total pulmonary resistance test (see Fleisch et al. and Boot et al., above). Measurement of bronchospasm was recorded as an increase in tracheal resistance produced by $LTD_4$ administered intravenously into anaesthetised artificially ventilated guinea pigs. Furthermore, compounds are active in the Guinea Pig Excised lung gas volume test (ELGV) (see Boot et al.) at doses of from 0.1 to 10 mg/kg. The ELGV test is based on an $LTD_4$-induced bronchospasm in guinea pigs which results in increased gas trapping within the lung and the compounds of the invention prevent such gas trapping.

The compounds of the invention also antagonise $LTD_4$ radioligand binding in guinea pig lung membranes in the test described by Saussy et al., Mol. Pharmacol. 39:72-78 1991, with a $pK_i$ of greater than 7.

The compounds of the invention are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever.

The compounds of the invention also have potential in the treatment of vascular diseases such as shock and ischaemic heart diseases for example coronary artery disease and myocardial infarction, cerebrovascular diseases, and renal diseases for example renal ischaemia.

Thus the invention also includes a pharmaceutical composition comprising a pharmaceutically acceptable diluent or carrier in association with a compound of formula (I) in unprotected form; or a pharmaceutically acceptable salt thereof.

The compounds may be administered by various routes, for example by the oral or rectal route, topically or parenterally, for example by injection or infusion, and especially by inhalation, being usually employed in the form of a pharmaceutical composition. Such compositions are prepared in a manner well known in the pharmaceutical art and comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc magnesium stearate and mineral oil. The compositions of the injection may, as is well known in the art, be formulated so as to provide quick, sustained or delayed release of the active ingredient after administration to the patent.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples.

EXAMPLE 1

5-<1-[3-{2(E)-(Quinolin-2-yl)ethenyl}benzyl]indol-7-yloxy methyl>-1H-tetrazole hydrochloride a) 7-Cyanomethoxy indole i) 2-(Benzyloxy)nitrobenzene A stirred mixture of 2-nitrophenol (13.9 g, 0.10 mol), benzyl bromide (12.0 ml, 0.10 mol) and anhydrous potassium carbonate (30 g, 0.22 mol) in acetone (200 ml) was heated under reflux for 16 hours, cooled, poured onto ice-dilute hydrochloric acid, and extracted with dichloromethane. The extract was dried and evaporated and the residue was crystallised from ether-hexane as pale crystals, m.p. <50° C.

ii) 2-(Benzyloxy)-aniline

Hydrazine hydrate (5 ml) was added dropwise over 20 minutes to a stirred suspension of Raney nickel in a solution of 2-(benzyloxy)nitrobenzene in methanol (200 ml) causing gentle reflux. The stirred mixture was heated under reflux for a further 30 minutes, cooled, filtered and evaporated. The residue was distilled under vacuum to give a pale oil, b.p. 146°–150°/0.5 mm.

iii) 2-Benzyloxy-6-(2,2-dimethoxy-1-methylthio)ethyl aniline

A solution of 2-methylthioacetaldehyde dimethyl acetal (4.9 g, 36.1 mmol) in dichloromethane (10 ml) was added dropwise to a stirred solution of chlorine (2.6 g, 36.1 mmol) in dichloromethane (70 ml) at −70° C. The solution was stirred at −70° to −76° C. for 15 minutes then a solution of 2-(benzyloxy)aniline (7.2 g, 36.1 mmol) in dichloromethane (20 ml) was added over 1 hour at ca −70° C. The dark mixture was stirred for a further 2 hours at −70° to −75° C. then triethylamine (7 ml) was added and the mixture was allowed to warm to room temperature. After stirring for a further 1 hour the mixture was washed successively with dilute hydrochloric acid and aqueous sodium bicarbonate solution, dried and evaporated. Chromatography of the residue on silica in ethyl acetate-hexane (1:4) gave the product contaminated with ca 15% of 2-(benzyloxy)aniline.

iv) 7-(Benzyloxy)-3-(methylthio)indole

A solution of crude 2-benzyloxy-6-(2,2-dimethoxy-1-methylthio)ethylaniline (6.0 g) in ethyl acetate (100 ml) was stirred with 2M hydrochloric acid for 7 hours. The ethyl acetate layer was washed with further dilute hydrochloric acid then with sodium bicarbonate solution, dried and evaporated. The residue was chromatographed on silica in ethyl acetate-hexane (1:8) to give a pale solid.

v) 7-(Benzyloxy)indole

Wet Raney nickel was added in portions to a stirred refluxing solution of 7-(benzyloxy)-3-(methylthio)indole (4.0 g, 14.9 mmol) in ethyl acetate (100 ml) and ethanol (60 ml) until all the starting material had been consumed (by RP HPLC). The mixture was filtered, the filtrate evaporated and the residue chromatographed on silica in ethyl acetate-hexane (1:8) to give a pale oil.

vi) 7-(Cyanomethoxy)indole

A solution of 7-benzyloxyindole (0.5 g, 2.24 mmol) in methanol (100 ml) was hydrogenated at 60 psi over 10% palladium on charcoal (50 mg) for 4 hours. The catalyst was filtered off and the filtrate was evaporated. A stirred solution of the residue and bromoacetonitrile (0.16 ml, 2.3 mmol) in methyl ethyl ketone (5 ml) was heated under reflux with solid anhydrous potassium carbonate (0.62 g, 4.5 mmol) for 2 hours, cooled, poured onto ice-hydrochloric acid and extracted with dichloromethane. The extract was dried and evaporated and the residue was chromatographed on silica in ethyl acetate-hexane (1:2) to give a pale solid.

b) 3-[2(E)-(Quinolin-2-yl)ethenyl]benzyl chloride i) Methyl 3-[2(E)-(quinolin-2-yl)ethenyl]benzoate 2.5M Butyl lithium in hexane (8.8 ml) was added over 5 minutes to a stirred solution of quinolin-2-ylmethylphosphonium chloride (9.66 g, 22 mmol) in dry tetrahydrofuran (250 ml) at −75° C. The mixture was stirred for 1 hour at −75° C. then a solution of methyl 3-formylbenzoate (3.28 g, 20 mmol) in tetrahydrofuran (25 ml) was added dropwise over 10 minutes. After stirring for a further 30 minutes at −75° C. the mixture was warmed to room temperature, diluted with water and extracted with ethyl acetate. The extract was dried and evaporated and the residue was purified by chromatography on silica eluting with ethyl acetate-hexane (1:3).

ii) 3-[2(E)-(Quinolin-2-yl)ethenyl]benzyl alcohol

Solid lithium aluminium hydride (0.25 g) was added in portions to a stirred solution of methyl 3-[2(E)-(quinolin-2-yl)ethenyl]benzoate (2.1 g, 7.3 mmol) in tetrahydrofuran (50 ml). The mixture was stirred for 30 minutes, diluted with sodium hydroxide solution and extracted with ethyl acetate. The extract was dried and evaporated and the residue was chromatographed on silica in ethyl acetate-hexane (1:1).

iii) 3-[2(E)-(Quinolin-2-yl)ethenyl]benzyl chloride

Solid N-chlorosuccinimide (0.76 g, 5.72 mmol) was added in portions over 5 minutes to a stirred solution of 3-[2(E)-(quinolin-2-yl)ethenyl]benzyl alcohol (1.14 g, 4.58 mmol) and triphenylphosphine (1.50 g, 5.72 mmol) in dichloromethane (100 ml) at 0°-5° C. The mixture was stirred for a further 2 hours at 0°-5° C. then evaporated and the residue was chromatographed on silica in ethyl acetate-hexane (1:3).

c) i)

1-[3-{2(E)-(Quinolin-2-yl)ethenyl}benzyl]indol-7-yloxyacetonitrile

60% Sodium hydride dispersion in mineral oil (48 mg, 1.2 mmol) was added in portions over 5 minutes to a stirred solution of 7-cyanomethoxyindole (Example 1a) (0.17 g, 1.0 mmol) in tetrahydrofuran (2 ml) and dimethylformamide (2 ml) at 0°-5° C. The mixture was stirred for 10 minutes at 0°-5° C. then a solution of 3-[2(E)-(quinolin-2-yl)ethenyl]benzyl chloride (Example 1b) (0.28 g, 1.0 mmol) in tetrahydrofuran (2 ml) was added dropwise over 5 minutes. The mixture was stirred for 3 hours at room temperature, diluted with water and extracted with ethyl acetate. The extract was washed with water, dried and evaporated and the residue was chromatographed on silica in ethyl acetate-hexane (1:9 to 1:3).

ii)

5-<1-[3-{2(E)-(Quinolin-2-yl)ethenyl}benzyl]indol-7-yloxymethyl>-1H-tetrazole hydrochloride A stirred solution of the nitrile (Example 1c part i) (0.19 g, 0.47 mmol) and tributyltin azide (0.23 g, 0.71 mmol) in tetrahydrofuran (5 ml) was heated under reflux for 16 hours then the solvent was allowed to evaporate and the residue was heated on an oil bath at 110° C. for 3 hours. The residue was dissolved in ethyl acetate and stirred with 2M hydrochloric acid to precipitate a gum. The liquid was decanted and the gum was washed with ether and crystallised from methanol, m.p. 145°-6° C.

NMR (300 MHz, $(CD_3)_2SO$) $\delta$5.52 (2H,s, $CH_2O$), 5.65 (2H, s, $CH_2N$), 6.51 (1H, indole 3-H), 7.41, 7.90 (two 1H, d, CH=CH). MS M=458.

EXAMPLE 2

5-<5-Carboxy-1-[3-{2(E)-(quinolin-2-yl)ethenyl}benzyl]indol-7-yloxymethyl>-1H-tetrazole a) 7-Cyanomethoxy-5-(methoxycarbonyl)indole This compound was prepared from 5-methoxycarbonyl-2-nitrophenol by the sequence of reactions described in Example 1a.

b) i)

5-<1-[3-{2(E)-Quinolin-2-yl)ethenyl}benzyl]-5-methoxycarbonylindol-7-yloxymethyl>1H-tetrazole This compound was prepared from 7-cyanomethoxy-5-(methoxycarbonyl)indole (Example 2a) and 3-[2(E)-(quinolin-2-yl)-ethenyl]benzyl chloride (Example 1b) by the methods described in Example 1c.

ii)

5-<5-Carboxy-1-[3-{2(E)-(quinolin-2-yl)ethenyl}benzyl]indol-7-yloxymethyl>-1H-tetrazole A solution of the methyl ester (Example 2b, part i) (95 mg) in tetrahydrofuran (4 ml) was stirred with M lithium hydroxide solution (4 ml) for 5 hours at room temperature then 16 hours at 45°-50° C. The mixture was concentrated to remove tetrahydrofuran, diluted with water and washed with ethyl acetate. The aqueous phase was acidified and evaporated to dryness and the residue was washed with methanol-water to give the product m.p. ca 230° C. (dec).

NMR (300 MHz, $(CD_3)_2SO$) $\delta$5.62 (2H, s, $CH_2O$), 5.68 (2H, s, $CH_2N$) 6.68 (1H, indole 3-H). MS M=502.

EXAMPLE 3

5-<4-Chloro-1-[3-{2(E)-(quinolin-2-yl)ethenyl}benzyl]indol-7-yloxymethyl>-1H-tetrazole a) 4-Chloro-7-(cyanomethoxy)indole i) 2-Benzyloxy-5-chloronitrobenzene 60% Sodium hydride dispersion in oil (4.4 g, 0.11 mol) was added in portions over 15 minutes to a stirred solution of 4-chloro-2-nitrophenol (17.4 g, 0.10 mol) in dimethylformamide (200 ml) at 0°-5° C. The mixture was stirred for 15 minutes then benzyl chloride (12.7 g, 0.10 mol) was added dropwise over 5 minutes. The mixture was stirred for 5 days at room temperature, diluted with water and extracted with ether. The extract was washed three times with water, dried and evaporated and the residue was triturated with petroleum spirit.

ii) 7-Benzyloxy-4-chloroindole

M Vinyl magnesium bromide solution in tetrahydrofuran (80 ml) was added to a stirred solution of 2-benzyloxy-5-chloronitrobenzene (5.28 g, 20 mmol) in tetrahydrofuran (160 ml) at −40° C. The mixture was stirred for 2 hours at −40° C. then poured onto saturated ammonium chloride solution (500 ml) and extracted with ether. The extract was dried and evaporated and the residue was chromatographed on silica in ethyl acetate-hexane (1:8) to give a yellow oil.

iii) 4-Chloro-7-(cyanomethoxy)indole

This compound was prepared from 7-benzyloxy-4-chloroindole (1.61 g, 6.24 mmol) by the method described in Example 1a part vi.

b)

5-<4-Chloro-1-[3-{2(E)-(quinolin-2-yl)ethenyl}benzyl]indol-7-yloxymethyl>-1H-tetrazole This compound was prepared from 4-chloro-7-(cyanomethoxy)indole and 3-[2(E)-(quinolin-2-yl)ethenyl]benzyl chloride (Example 1b) by the methods described in Example 1c. After completion of the reaction the product was dissolved in methanol and acidified with 2M hydrochloric acid. Crystals of the product formed slowly, m.p. 260° (dec).

Anal. C, 68.05; H, 4.37; N, 17.07; Cl, 7.37% ($C_{28}H_{21}ClN_6O$ requires C, 68.22; H, 4.29; N, 17.05; Cl 7.19%).

NMR (300 MHz, $(CD_3)_2$ SO) $\delta$5.55 (2H, s, $CH_2N$), 5.64 (2H, s, $CH_2O$) 6.53 (1H, indole 3-H), 7.35, 7.69 (two 1H, d, —CH=CH). MS M=492/494.

EXAMPLE 4

5-<4-Carboxy-1-{3-[2(E)-(quinolin-2-yl)ethenyl]benzyl}indol-7-yloxymethyl>-1H-tetrazole a) 7-Cyanomethoxy-4-(methoxycarbonyl)indole

This compound was prepared from 4-methoxy-carbonyl-2-nitrophenol by the methods described in Examples 1a part i, 3a part ii, and 1a part vi.

5-<4-Carboxy-1-{3-[2(E)-(quinolin-2-yl)ethenyl]benzyl}indol-7-yloxymethyl>-1H-tetrazole This compound was prepared from 7-cyanomethoxy-4-(methoxycarbonyl)indole (Example 4a) and 3-[2(E)-(quinolin-2-yl)ethenyl]benzyl chloride (Example 1b) by the methods described in Examples 1c and 2b part ii. The reaction mixture was acidified with 2M hydrochloric acid to give a yellow solid which was washed with water, methanol and ethyl acetate, m.p. ca 200° C. (dec).

NMR (300 MHz, $(CD_3)_2 SO$) $\delta$5.61 (2H, s, $CH_2O$), 5.65 (2H, s, $CH_2N$), 7.05 (1H, indole 3-H), 7.36, 7.69 (two 1H, d, CH=CH). MS M=502.

EXAMPLE 5

5-<1-[3-(Quinolin-2-ylmethoxy)benzyl]indol-7-yloxymethyl>-1H-tetrazole a) 3-(Quinolin-2-ylmethoxy) benzyl chloride i) 3-(Quinolin-2-ylmethoxy)benzyl alcohol 60% Sodium hydride dispersion in oil (0.70 g, 17.5 mmol) was washed with hexane under nitrogen and suspended in dry tetrahydrofuran (30 ml). A solution of 3-hydroxymethylphenol (2.14 g, 17.2 mmol) in dry dimethylformamide was added dropwise to the stirred suspension at 5°-10° C. and the mixture was stirred for 30 minutes at room temperature. A solution of 2-chloromethylquinoline (3.07 g, 17.2 mmol) in tetrahydrofuran (10 ml) was added dropwise and the mixture was stirred for 22 hours at room temperature and 7 hours at 40° C. then poured onto saturated ammonium chloride solution (100 ml) and extracted with dichloromethane. The extract was washed with water, dried and evaporated to a viscous oil which crystallised from ethyl acetate-hexane, m.p. 70° C.

ii) 3-(Quinolin-2-ylmethoxy)benzyl chloride

This compound was prepared from 3-(quinolin-2-ylmethoxy)benzyl alcohol by the method described in Example 1b part iii.

b) i)

1-[3-(Quinolin-2-ylmethoxy)benzyl]indol-7-yloxyacetonitrile

This compound was prepared from 7-cyanomethoxyindole (Example 1a) and 3-(quinolin-2-ylmethoxy)benzyl chloride (Example 5a) by the method described in Example 1c.

ii)

5-<1-[3-(Quinolin-2-ylmethoxy)benzyl]indol-7-yloxymethyl>-1H-tetrazole

A stirred solution of the nitrile (Example 5b part i) (0.29 g, 0.69 mmol) and tributyltin azide (0.34 g, 1.02 mmol) in dimethoxyethane (8 ml) was heated under reflux for 16 hours. The solvent was allowed to evaporate and the residue was heated at ca 100° C. for 1 hour then dissolved in methanol (10 ml) and 2M hydrochloric acid (1 ml). The solution was evaporated and the residue crystallised from methanol, m.p. 157° C.

NMR (300 MHz, $(CD_3)_2 SO$) $\delta$5.23 (2H, s, quinoline $CH_2O$), 5.46 (2H, s, tet $CH_2O$), 5.54 (2H, s, $CH_2N$), 6.41 (1H, indole 3-H). MS M=462.

EXAMPLE 6

5-<1-{3-[2(E)-(7-Chloroquinolin-2-yl)ethenyl]benzyl}indol-7-yloxymethyl>-1H-tetrazole hydrochloride a) 3-[2(E)-(7-Chloroquinolin-2-yl)ethenyl]benzyl chloride i) 3-[2(E)-(7-Chloroquinolin-2-yl)ethenyl]benzaldehyde A stirred solution of 7-chloroquinaldine [J. Org. Chem. 42, 911 (1977)] (4.46 g, 25 mmol) and isophthalaldehyde (5.02 g, 37.5 mmol) in acetic anhydride (7.1 ml, 75 mmol) and xylene (25 ml) was heated under reflux for 7 hours. Crystals formed on cooling. Hexane (25 ml) was added slowly to give crude product, m.p. 146°-150°.

ii) 3-[2(E)-(7-Chloroquinolin-2-yl)ethenyl]benzyl alcohol

Solid sodium borohydride (2.5 g) was added in portions to a stirred suspension of crude 3-[2(E)-(7-chloroquinolin-2-yl)ethenyl]benzaldehyde (5.8 g) in methanol (200 ml). The mixture was filtered and the filtrate was concentrated to ca 70 ml and diluted with hot water to give crystals, m.p. 141° C.

iii) 3-[2(E)-(7-Chloroquinolin-2-yl)ethenyl]benzyl chloride

This compound was prepared from 3-[2(E)-(7-chloroquinolin-2-yl)ethenyl]benzyl alcohol by the method described in Example 1b part iii. The crude product was extracted with ethyl acetate (leaving an insoluble impurity) and passed through a silica column washing through with further ethyl acetate. Evaporation of the ethyl acetate gave moderately pure product.

5-<1-{3-[2(E)-(7-Chloroquinolin-2-yl)ethenyl]benzyl}indol-7-yloxymethyl>-1H-tetrazole hydrochloride This compound was prepared from 7-cyano-methoxyindole (Example 1a) and 3-[2(E)-(7-chloroquinolin-2-yl)ethenyl]benzyl chloride (Example 6a) by the methods described in Example 1c. The crude reaction product was dissolved in methanol and acidified with 2M hydrochloric acid to give yellow crystals of the hydrochloride salt which were washed with ethyl acetate and methanol, m.p. ca 200° C.

NMR (300 MHz, $CD_3OD$) $\delta$5.34 (2H, s, $CH_2N$), 5.65 (2H, s, $CH_2O$), 6.52 (1H, indole 3-H), 7.30, 8.00 (two 1H, d, CH=CH). MS M=492/494.

EXAMPLE 7

5-<4-Chloro-1-{3-[2(E)-(7-chloroquinolin-2-yl)ethenyl]benzyl}indol-7-yloxymethyl>-1H-tetrazole

This compound was prepared from 4-chloro-7-(cyanomethoxy)indole (Example 3a) and 3-[2(E)-(7-chloroquinolin-2-yl)ethenyl]benzyl chloride (Example 6a) by the methods described in Examples 1c part i and 5b part ii. The zwitterionic product crystallised from the acidified methanol solution, m.p. 154° C.

NMR (300 MHz, $(CD_3)_2SO$) $\delta$5.55 (2H, s, $CH_2O$), 5.66 (2H, s, $CH_2N$), 6.54 (1H, indole 3-H), 7.39, 7.81 (two 1H, d, CH=CH). MS M=526/528/530.

EXAMPLE 8

5-<1-[4-{2(E)-(Quinolin-2-yl)ethenyl}benzyl]indol-7-yloxymethyl>-1H-tetrazole hydrochloride a) 4-[2(E)-(Quinolin-2-yl)ethenyl]benzyl chloride

This compound was prepared from quinaldine and terephthalaldehyde by the methods described in Examples 6a parts i and ii and 1b part iii.

5-<1-[4-{2(E)-(Quinolin-2-yl)ethenyl}benzyl]indol-7-yloxymethyl>-1H-tetrazole hydrochloride This compound was prepared from 7-(cyanomethoxy)indole (Example 1a) and 4-[2(E)-(quinolin-2-yl)ethenyl]benzyl chloride (Example 8a) by the methods described in Examples 1c part i and 5b part ii. The hydrochloride salt crystallised from methanol- HCl, m.p. 164°–166° C.

NMR (300 MHz, $(CD_3)_2$ SO) δ5.47 (2H, s, $CH_2O$), 5.63 (2H, s, $CH_2N$), 6.50 (1H, indole 3-H), 7.52, 8.07 (two 1H, d, CH=CH). MS M=458.

EXAMPLE 9

5-<1-[3-(7-Chloroquinolin-2-ylmethoxy)benzyl]indol-7-yloxymethyl>-1H-tetrazole a) 3-(7-Chloroquinolin-2-ylmethoxy)benzyl chloride i) 7-Chloro-2-chloromethylquinoline

N-Chlorosuccinimide (3.0 g, 22.5 mmol) was added in portions over 1 hour to a stirred solution of 7-chloroquinaldine (3.3 g, 18.5 mmol) and dibenzoyl peroxide (0.1 g) in carbon tetrachloride (100 ml) under reflux. The mixture was heated under reflux for 24 hours adding further N-chlorosuccinimide (0.5 g and 1.0 g) after 3 hours and 20 hours. The mixture was cooled and filtered and the filtrate was extracted with 2M hydrochloric acid (5×40 ml). The extract was basified and re-extracted with dichloromethane and the extract was dried and evaporated to give the product contaminated with 7-chloroqinaldine.

ii) 3-(7-Chloroquinolin-2-ylmethoxy)benzyl chloride

This compound was prepared from 7-chloro-2-chloromethylquinoline by the methods described in Examples 5a part i (with purification of the product by chromatography on silica in ethyl acetate-hexane) and 1b part (iii).

b) 5-<1-[3-(7-Chloroquinolin-2-ylmethoxy)benzyl]indol-7-yloxymethyl>-1H-tetrazole This compound was prepared from 7-(cyanomethoxy)indole (Example 1a) and 3-(7-chloroquinolin-2-ylmethoxy)benzyl chloride (Example 9a) by the methods described in Examples 1c part i and 5b part ii purifying the final product by reverse phase HPLC on C-18 silica in methanol-water-acetic acid (80/20/0.1), m.p. 165° C.

NMR (300 MHz, $(CD_3)_2$ SO) δ5.24 (2H, s, quinoline $CH_2O$), 5.44 (2H, s, tet $CH_2O$), 5.54 (2H, s, $CH_2N$), 6.40 (1H, indole 3-H). MS M=496/498.

EXAMPLE 10

5-<2-[1-{3-(2-(E)-(Quinolin-2-yl)ethenyl)benzyl}indol-7-yl]ethyl>-1H-tetrazole a) 7-(2-Cyanoethyl)indole i) Methyl 3-[2-(E)-(dimethylamino)ethenyl]-2-nitrobenzoate

A solution of methyl 3-methyl-2-nitrobenzoate (43 g, 0.22 mole), dimethylformamide dimethyl acetal (52.5 g, 0.44 mole) and piperidine (18.7 g, 0.22 mole) in dimethylformamide (120 ml) was heated under reflux for 24 hours, cooled and poured into water to give the crude product.

ii) Methyl 7-indolecarboxylate

A solution of methyl 3-[2-(E)-(dimethylamino)ethenyl]-2-nitrobenzoate (12.0 g, 48 mmol) in toluene (200 ml) was hydrogenated at 60 psi over 10% palladium on charcoal (1.5 g) until hydrogen uptake ceased. The catalyst was filtered off, the filtrate was evaporated and the residue was chromatographed on silica to give the product.

iii) 7-Indole methanol

Solid lithium aluminum hydride (1.0 g) was added in portions over 1 hour to a stirred solution of methyl 7-indolecarboxylate (6.7 g) in tetrahydrofuran (100 ml). The mixture was stirred for a further 2 hours then excess lithium aluminium hydride was destroyed by addition of acetic acid, the mixture was diluted with aqueous sodium hydroxide and extracted with ethyl acetate. The extract was dried and evaporated and the residue was chromatographed on silica in ethyl acetate-hexane (1:9 to 1:2) to give the product.

iv) 7-Indolecarboxaldehyde

Solid pyridinium dichromate (1.77 g, 5.1 mmol) was added in portions over 3 hours to a stirred solution of 7-indolemethanol (0.5 g, 3.4 mmol) in dichloromethane (50 ml). The mixture was stirred for a further 2 hours then filtered through a pad of Celite filter aid. The filtrate was evaporated and the residue purified by chromatography on silica in ethyl acetate-hexane (1:3).

v) 7-[2-(E)-Cyanoethenyl]indole

Sodium hydride, 60% dispersion in mineral oil (0.10 g, 2.5 mmol) was added in portions over 10 minutes to a stirred solution of diethyl cyanomethylphosphonate (0.44 g, 2.5 mmol) in tetrahydrofuran (10 ml) cooled in ice. The mixture was stirred for 15 minutes then a solution of 7-indole carboxaldehyde (0.30 g, 2.1 mmol) in tetrahydrofuran (2 ml) was added dropwise. The mixture was stirred for 30 minutes, diluted with ethyl acetate, washed with water, dried and evaporated. The residue was chromatographed on silica in ethyl acetate-hexane (1:3) to give the product.

vi) 7-(2-Cyanoethyl)indole

A solution of 7-[2-(E)-cyanoethenyl]indole (0.28 g) in ethanol (75 ml) was hydrogenated at 50 psi over 10% palladium on charcoal (0.1 g) for 4 hours. The catalyst was filtered off and the filtrate was evaporated to give the product.

b)
5-<2-[1-{3-(2-(E)-(Quinolin-2-yl)ethenyl)benzyl}indol-7-yl]ethyl>-1H-tetrazole This compound was prepared from 7-(2-cyanoethyl)indole and 3-[2-(E)-(quinolin-2-yl)ethenyl]benzyl chloride (Example 1b) by the methods described in Example 1c. The crude hydrochloride salt crystallised from methanol and was converted to the zwitterionic form by stirring with 10% ammonium hydroxide solution and washing with hot chloroform, m.p. 182°-185° C.

NMR (300 MHz, (CD$_3$)$_2$ SO) δ3.09, 3.27 (two 2H, t, CH$_2$—CH$_2$), 5.72 (2H, s, CH$_2$N), 6.60 (1H, indole 3-H), 7.35, 7.70 (two 1H, d, CH=CH). MS M=456.

EXAMPLE 11

5-<4-Trifluoromethyl-1-[3-{2(E)-(7-chloroquinolin-2-yl)ethenyl}benzyl]indol-7-yloxymethyl>-1H-tetrazole a) 7-Cyanomethoxy-4-trifluoromethylindole This compound was prepared from 2-nitro-4-trifluoromethylphenol by the methods described in Examples 1a part (i), 3a part (ii) and 1a part (vi).

b)
5-<4-Trifluoromethyl-1-[3-{2(E)-(7-chloroquinolin-2-yl)ethenyl}benzyl]indol-7-yloxymethyl>-1H-tetrazole This compound was prepared from 7-cyanomethoxy-4-trifluoromethylindole (Example 11a) and 3-[2(E)-(7-chloroquinolin-2-yl)ethenyl]benzyl chloride (Example 6a, by the methods described in Examples 1c part (i) (using only dimethylformamide as solvent) and 5b part (ii), m.p. ca 240° C. (dec).

NMR (300 MHz, (CD$_3$)$_2$SO) δ5.61 (2p, s, CH$_2$O), 5.68 (2p, s, CH$_2$N), 6.60 (1p, indole 3H), 7.43, 7.87 (two 1p, d, CH=CH). MS M=560/562.

EXAMPLE 12

1-[3-{2(E)-(7-Chloroquinolin-2-yl)ethenyl}benzyl]indol-7-yl-oxyacetic acid a) 7-Trityloxyindole This compound was prepared from 2-nitrophenol by the methods described in Examples 1a part (i) and 3a part (ii).

b) i)
1-[3-{2(E)-(7-Chloroquinolin-2-yl)ethenyl}benzyl]-7-trityloxy-indole

60% Sodium hydride dispersion in mineral oil (44 mg 1.1 mmol) was added to a stirred solution of 7-trityloxyindole (Example 12a) (375 mg, 1.0 mmol) in dimethylformamide (4 ml). The mixture was stirred for 10 minutes at room temperature then a suspension of 3-[2(E)-(7-chloroquinolin-2-yl)ethenyl]benzyl chloride (Example 6a) (251 mg, 0.80 mmol) in dimethylformamide (4 ml) was added and the mixture was stirred for a further 3 hours. The dark solution was poured onto saturated ammonium chloride solution and extracted with dichloromethane. The extract was dried and evaporated under high vacuum and the residue was chromatographed on silica in ethyl acetate-hexane (1:5).

ii) Methyl
1-[3-{2-(E)-(7-chloroquinolin-2-yl)ethenyl}benzyl]indol-7-yloxyacetate A solution of the trityloxy compound (Example 12b part (i)) (0.50 g., 0.76 mmol) and trifluoroacetic acid (0.12 ml, 1.56 mmol) in methyl ethyl ketone (7 ml) was stirred at room temperature for 2 hours. Methyl bromoacetate (0.09 ml., 0.97 mmol) and anhydrous potassium carbonate (0.40 g., 3.0 mmol) were added and the stirred mixture was heated under reflux for 2 hours. The mixture was poured onto saturated ammonium chloride solution and extracted with dichloromethane. The extract was dried and evaporated and the residue was chromatographed on silica in ethyl acetate-hexane (1:4) to give the product contaminated with a trityl containing impurity.

iii)
1-[3-{2(E)-(7-Chloroquinolin-2-yl)ethenyl}benzyl]-indol-7-yl-oxyacetic acid A solution of the crude methyl ester (Example 12b part (ii) (0.27 g) in tetrahydrofuran (5 ml), methanol (3 ml) and 0.5M potassium carbonate solution (5 ml) was stirred at room temperature for 16 hours, then acidified with acetic acid, concentrated, and diluted with water to precipitate a pale solid. The product was purified by RPHPLC on a C-18 column eluting with 70 methanol/30 water/0.1 triethylamine/0.1 ammonium acetate. The product-containing eluate was concentrated and acidified with acetic acid to give a yellow solid. m.p. 240° C.

NMR/300 MHz, (CD$_3$)$_2$SO) δ4.71 (2p, s, CH$_2$O), 5.71 (2p, s, CH$_2$N), 6.45 (1p, indole 3H), 7.34, 7.67 (two 1p, d, CH=CH). MS M=468/470.

EXAMPLE 13

5-<1-{3-[2(E)-(Quinolin-2-yl)ethenyl]benzyl}indol-7-ylmethyl>-1H-tetrazole, hydrochloride a)
1-[3-{2(E)-(Quinolin-2-yl)ethenyl}benzyl]indole-7-carboxaldehyde A solution of 7-formyl indole (Example 10a (iv) (2 g, 13.8 mmole) in dry dimethyl formamide (40 ml) was cooled in an ice bath and stirred as sodium hydride (60% dispersion in mineral oil) (0.66 g, 16.5 mmole) was added in portions over 10 minutes. The mixture was stirred for a further 30 minutes, then a solution of 3-[2-(E)-quinolin-2-yl ethenyl]benzyl chloride (Example 1b) (4.24 g, 15.2 mmole) in dry THF (12 ml) was added over 2 minutes. The reaction mixture was stirred at room temperature for 3 days, then poured into water, extracted into ethyl acetate, dried and evaporated. The residue was chromatographed on silica, eluting with ethyl acetate-hexane (1:3) to give the product.

b) i)
1-[3-{2(E)-(Quinolin-2-yl)ethenyl}benzyl]indol-7-ylacetonitrile

A solution of p-toluenesulphonylmethyl isocyanide (165 mg., 0.85 mmol) in 1,2-dimethoxyethane (1 ml) was added to a stirred suspension of potassium t-butoxide (205 mg, 1.68 mmol) in 1,2-dimethoxyethane (1 ml) at ca −50° C. under nitrogen. The mixture was allowed to warm to ca −30° C. then cooled to −60° C. and a solution of 1-[3-{2(E)-(quinolin-2-yl)ethyl}benzyl]indol-7-carboxaldehyde (Example 13a) (320 mg., 0.82 mmol) in 1,2-dimethoxyethane (1.5 ml) was added. The dark solution was stirred at ca −60° C. for 1 hour then methanol (2 ml) was added and the solution was heated under reflux for 10 minutes and evaporated. The residue was treated with water (10 ml) and acetic acid (0.5 ml) and extracted with dichloromethane. The extract was dried and evaporated and the redidue was chromatographed on silica in ethyl acetate-hexane (1:3).

ii)

5-<1-{3-[2(E)-(Quinolin-2-yl)ethenyl]benzyl}indol-7-ylmethyl>-1H-tetrazole

A stirred solution of the nitrile (Example 13c part (i)) (0.43 g, 1.08 mmol) and tributyl tin azide (0.54 g, 1.63 mmol) in diglyme (8 ml) was heated at 140°-150° C. for 6 hours. The solution was evaporated under high vacuum and the residue in methanol (15 ml) was acidified with 2M hydrochloric acid (1.5 ml). A little dark tar formed. The clear supernatant was decanted neutralised with 2M sodium hydroxide and diluted with water to precipitate the product which was washed with ethyl acetate, m.p. 228° C.

NMR (300 MHz, (CD$_3$)$_2$SO) δ4.42 (2p, s, CH$_2$-Tet), 5.75 (2p, s, CH$_2$N), 6.62 (1p, indole 3H), 7.38, 7.75 (two 1p, d, CH=CH). MS M=442.

EXAMPLE 14

5-<2-[1-{3-(2(E)-(7-Chloroquinolin-2-yl)ethenyl)benzyl}indol-7-yl]ethyl>-1H-tetrazole hydrochloride a) 7-(2-Cyanoethyl)indole i) 7-Formyl indole

A solution of 7-bromoindole [Tet. Lett. 30, 2129 (1989)] (12.75 g, 0.065 mole) in dry tetrahydrofuran (230 ml) was cooled in a dry ice-acetone bath and 2.5M n-butyl lithium in hexane (78 ml, 0.195 mole) added dropwise over 1 hour, maintaining the reaction temperature below −60° C. The reaction mixture was stirred for a further 15 minutes at −70° C., then allowed to warm to 5° C. After 30 minutes at 5° C., the reaction was recooled to −70° C. and dimethylformamide (25 ml, 0.325 mole) added dropwise at a rate to maintain the temperature below −65° C. The mixture was allowed to warm to room temperature slowly, then was poured into water and extracted into diethyl ether. The combined dry extracts were washed with brine, dried and evaporated. Recrystallisation from 80°-100° C. petroleum ether with charcoal treatment yielded the product as fawn-coloured crystals.

ii) 7-[2-(E)-Cyanoethenyl]indole

This compound was prepared from 7-formylindole by the method described in Example 10a, part (v). Crude product after-work-up was recrystallised from hot toluene.

iii) 7-(2-Cyanoethyl)indole

This compound was prepared from 7-[2-(E)-cyanoethenyl]indole by the method described in Example 10a, part (vi).

b) 3-[2(E)-(7-Chloroquinolin-2-yl)ethenyl]benzyl chloride

Thionyl chloride (3.6 ml., 49.3 mmol) was added rapidly to a stirred solution of 3-[2(E)-(7-chloroquinolin-2-yl)ethenyl]benzyl alcohol (Example 6a part (ii)) (11.7 g, 39.5 mmol) in 1,2-dichloroethane (300 ml) at 50° C. giving an immediate yellow precipitate. The mixture was stirred for 1 hour and cooled to room temperature then the mixture was shaken with saturated sodium bicarbonate solution (400 ml) and methanol (50 ml) to give two clear phases. The aqueous phase was extracted with dichloromethane and the combined solvent phase was dried and evaporated.

c) i)

7-(2-Cyanoethyl)-1-[3-{2(E)-(7-chloroquinolin-2-yl)ethenyl}benzyl]indole

A solution of 7-(2-cyanoethyl)indole (Example 14a) (4.42 g, 26 mmol) in dimethylformamide (30 ml) was added dropwise to a stirred suspension of sodium hydride (1.3 g, 60% dispersion, 32.5 mmol, washed with hexane under nitrogen) in dimethylformamide (30 ml) at 10°-15° C. The mixture was stirred for 15 minutes at ca 15° C. then a suspension of 3-[2(E)-(7-chloroquinolin-2-yl)ethenyl] benzyl chloride (Example 14b) (10.2 g, 32.5 mmol) in dimethylformamide (60 ml) was added rapidly. The dark mixture was stirred for 5 hours at room temperature, poured onto saturated ammonium chloride solution and extracted with dichloromethane. The extract was dried and evaporated under high vacuum and the residue in dichloromethane (30 ml) was applied to a silica column and eluted with ethyl acetate-hexane (1:2). The product was recrystallised from ethyl acetate-hexane, m.p. 151° C.

ii)

5-<2-[1-{3-(2(E)-(7-chloroquinolin-2-yl)ethenyl)benzyl}indol-7-yl]ethyl>-1H-tetrazole hydrochloride A stirred mixture of the nitrile (Example 14c part (i)) (8.0 g, 18.1 mmol) and tributyl tin azide (8.0 g, 24.1 mmol) was heated at 150° C. under nitrogen for 1 hour. The viscous residue was dissolved in hot 1,2-dimethoxyethane (80 ml) and acidified with 2M hydrochloric acid (16 ml). Orange crystals formed on cooling, m.p. 231° C.

NMR (300 MHz, (CD$_3$)$_2$SO) δ3.1, 3.3. (two 2p, t, CH$_2$—CH$_2$-Tet), 5.71 (2p, s, CH$_2$N), 6.60 (1p, indole 3H), 7.35, 7.75 (two 1p, d, CH=CH). MS M=490–492 (i.e. HCl lost).

EXAMPLE 15

5-<3-[1-{3-(2(E)-(7-Chloroquinolin-2-yl)ethenyl)benzyl}indol-7-yl]propyl>-1H-tetrazole hydrochloride a) 7-(3-Cyanopropyl)indole i) 4-(2-Nitrophenyl)butyronitrile

4-Phenylbutyronitrile (12.7 g) was added dropwise to stirred concentrated nitric acid (55 ml) at 5°-10° C. and the mixture was stirred for 2 hours at 20°-25° C. The deep yellow solution was poured onto ice and extracted with dichloromethane. The extract was dried and evaporated and the residue was chromatographed on silica in ethyl acetate-hexane (1:4) to isolate the minor product.

ii) 7-(3-Cyanopropyl)indole

This compound was prepared by the method described in Example 3a part (ii).

b) i)

1-[3-{2(E)-(7-Chloroquinolin-2-yl)ethenyl}benzyl]-7-(3-cyanopropyl)indole

This compound was prepared from 7-(3-cyanopropyl)-indole (Example 15a) (0.40 g, 2.17 mmol) by the method described in Example 12b part (i).

ii)
5-<3-[1-{3-(2(E)-(7-Chloroquinolin-2-yl)ethenyl)benzyl}indol-7-yl]propyl>-1H-tetrazole hydrochloride The nitrile (Example 15b part (i)) was reacted with tributyl tin azide as described in Example 13b part (ii). The crude product was purified by RPHPLC on a C-18 column eluting with 70 methanol:30 water:0.1 triethyl amine:0.1 ammonium acetate. The eluate was concentrated and acidified with acetic acid to precipitate a pale solid which was washed with water and dried. The solid was dissolved in hot methanolic hydrochloric acid, decanted from a little dark tar and concentrated to give orange crystals, m.p. ca 155° C.

NMR (300 MHz, (CD$_3$)$_2$SO $\delta$1.97 (2p, CH$_2$CH$_2$CH$_2$), 2.81, 2.91 (two 2p, t, CH$_2$CH$_2$CH$_2$), 5.62 (2p, s, CH$_2$N), 6.59 (1p, indole 3H).

EXAMPLE 16

5-<1-[α-Phenyl-3-{2-(E)-(quinolin-2-yl)ethenyl}benzyl]indol-7-yloxymethyl>-1H-tetrazole a) α-Phenyl-3-[2-(E)-(quinolin-2-yl)ethenyl]benzyl chloride hydrochloride i) 3-[2-(E)-(Quinolin-2-yl)ethenyl]benzaldehyde This compound was prepared from quinaldine by the method described in Example 6a part (i).

ii)
α-Phenyl-3-[2-(E)-(quinolin-2-yl)ethenyl]benzylalcohol

A solution of 3-[2(E)-(quinolin-2-yl)ethenyl] benzaldehyde (5.9 g, 22.8 mmol) in tetrahydrofuran (20 ml) was added to a stirred solution of phenyl magnesium bromide [prepared from bromobenzene (4.3 g, 27.4 mmol) and magnesium turnings(0.66 g, 27.4 mg atom) in tetrahydrofuran (50 ml) at ca 40° C.] at 10°-15° C. The dark solution was stirred for 1 hour at room temperature, poured onto saturated ammonium chloride solution and extracted with dichloromethane. The extract was dried and evaporated and the residue was crystallised from ethyl acetate.

iii)
α-Phenyl-3-[2(E)-(quinolin-2-yl)ethenyl]benzyl-chloride hydrochloride

α-Phenyl-3-[2(E)-(quinolin-2-yl)ethyl]benzyl alcohol (5.09 g, 15.1 mmol) was dissolved in thionyl chloride (10 ml, 137 mmol) giving a warm yellow solution. The solution was allowed to cool to 30° C. and diluted slowly with ether (50 ml) to give a yellow solid.

b) i)
1-[α-Phenyl-3-{2(E)-(quinolin-2-yl)ethenyl}benzyl]indol-7-yloxyacetonitrile Powdered potassium hydroxide (0.24 g, 4.3 mmol) was added to a stirred solution of 7-cyanomethoxyindole (Example 1a)(0.34 g, 0.20 mmol) in dimethylsulphoxide (4 ml) under nitrogen. The dark solution was stirred for 15 minutes at room temperature then a suspension of α-phenyl-3-[2(E)-(quinolin-2-yl)ethenyl] benzyl chloride hydrochloride (Example 16a) (0.78 g, 2.0 mmol) in dimethylsulphoxide (5 ml) was added. The stirred mixture was heated at 50° C. for 4 hours, poured onto saturated ammonium chloride solution and extracted with dichloromethane. The extract was dried and evaporated and the residue was chromatographed on silica in ethyl acetate-hexane (1:3) to give a pale oil containing the product plus unreacted 7-cyanomethoxyindole. These were separated by RPHPLC on a C-18 column eluting with 90 methanol:10 water:0.1 acetic acid to give the product as a white solid.

ii)
5-<1-[α-Phenyl-3-{2(E)-(quinolin-2-yl)ethenyl}benzyl]indol-7-yloxymethyl>-1H-tetrazole The nitrile (Example 16b part (i)) was reacted with tributyl tin azide as described in Example 14c part (ii). The product in 1,2-dimethoxyethane (2 ml) was acidified with acetic acid (0.1 ml) and diluted with methanol (4 ml) to slowly give yellow solid, m.p. >260° C.

NMR (300 MHz, (CD$_3$)$_2$SO) 5.39 (2p, s, CH$_2$O), 7.31 (1p, s, CHN), 6.49 (1p, indole 3H), 7.40, 7.76 (two 1p, d, CH=CH). MS M=534.

EXAMPLE 17

5-<2-[1-{4-(2(E)-(7-Chloroquinolin-2-yl)ethenyl)benzyl}indol-7-yl]ethyl>-1H-tetrazole hydrochloride a) 4-[2(E)-(7-Chloroquinolin-2-yl)ethenyl]benzyl chloride This compound was prepared by the methods described in Example 6a.

b)
5-<2-[1-{4-(2(E)-(7-Chloroquinolin-2-yl)ethenyl)benzyl}indol-7-yl]ethyl>-1H-tetrazole hydrochloride This compound was prepared from 7-cyanoethyl indole (Example 10a) and 4-[2(E)-(7-chloroquinolin-2-yl)ethenyl]benzyl chloride by the methods described in Examples 12b part (i) and 5b part (ii). The crude product was washed with ether, dissolved in hot methanol and crystallised by addition of hydrochloric acid and cooling, m.p. ca 170° C. (dec.).

NMR (300 MHz, (CD$_3$)$_2$SO) $\delta$3.11, 3.22 (two 2p, t, CH$_2$CH$_2$ Tet), 5.71 (2p, s, CH$_2$N), 6.59 (1p, indole 3H), 7.48, 7.95 (two 1p, d, CH=CH). MS M=491/493 (i.e. HCl lost).

EXAMPLE 18

5-<4-(2-Carboxyethyl)-1-[3-{2(E)-(quinolin-2-yl)ethenyl}benzyl]-indol-7-yloxymethyl>-1H-tetrazole a) 7-Cyanomethoxy-4-(2-methoxycarbonylethyl)indole i) 7-Benzyloxyindole-4-methanol A solution of 7-benzyloxy-4-(methoxycarbonyl)indole (Example 4a) (2.08 g, 7.4 mmol) was added to a stirred suspension of lithium aluminium hydride (0.38 g, 10 mmol) in tetrahydrofuran (15 ml). The mixture was heated at 50° C. for 1 hour, poured onto ice-hydrochloric acid and extracted with dichloromethane. The extract was dried and evaporated and the residue was chromatographed on silica in ethyl acetate-hexane (1:2 then 1:1) to give a pale oil.

ii) 7-Benzyloxyindole-4-carboxaldehyde

Solid pyridinium dichromate (5.4 g., 15.5 mmol) was added in portions over 8 hours to a stirred solution of 7-benzyloxyindole-4-methanol (1.17 g, 4.6 mmol) in dichloromethane (30 ml). The dark mixture was stirred for a further 2 hours, filtered through a bed of silica and evaporated.

iii)
7-Benzyloxy-4-(2-(E)-methoxycarbonylethenyl)indole

60% Sodium hydride dispersion (0.10 g, 2.5 mmol) was added to a stirred solution of trimethylphosphonoacetate (0.41 ml, 2.5 mmol) in tetrahydrofuran (10 ml). The pale suspension was stirred for 1 hour at room temperature then a solution of 7-benzyloxyindole-4-carboxaldehyde (0.63 g, 2.5 mmol) in tetrahydrofuran (5 ml) was added followed by dimethylformamide (5 ml) to give a clear solution. The solution was stirred for 1 hour at room temperature then evaporated under high vacuum. The residue in ethyl acetate was washed with dilute hydrochloric acid dried and concentrated to give pale solid.

iv)
7-Cyanomethoxy-4-(2-methoxycarbonylethyl)indole

A suspension of 7-benzyloxy-4-(2(E)-methoxycarbonylethenyl)indole (0.50 g, 1.63 mmol) in methanol (40 ml) and ethyl acetate (10 ml) was hydrogenated at 60 p.s.i. over 10% palladium on charcoal (0.10 g) for 3 hours. The catalyst was filtered off and the filtrate was evaporated. A stirred solution of the residue and bromoacetonitrile (0.12 ml, 1.72 mmol) in methyl ethyl ketone was heated under reflux with solid anhydrous potassium carbonate (0.48 g, 3.4 mmol) for 3.5 hours, poured onto ice-hydrochloric acid and extracted with dichloromethane. The extract was dried and evaporated and the residue was chromatographed on silica in ethyl acetate-hexane (1:3) to give a pale solid.

b) i)
4-(2-Carboxyethyl)-1-[3-{2(E)-(quinolin-2-yl)ethenyl}-benzyl]indol-7-yloxyacetonitrile 7-Cyanomethoxy-4-(2-methoxycarbonylethyl)indole (0.15 g, 0.58 mmol) was reacted with 3-[2(E)-(quinolin-2-yl)ethenyl]benzyl chloride (0.16 g, 0.58 mmol) by the method described in Example 1c part (i). Chromatography of the crude product gave the acid (0.19 g) and the methyl ester (70 mg). A solution of the ester in tetrahydrofuran (3 ml) and M lithium hydroxide solution (3 ml) was stirred for 5 hours, acidified with acetic acid and concentrated to give further acid product.

ii)
5-<4-(2-Carboxyethyl)-1-[3-{2(E)-(quinolin-2-yl)-ethenyl}benzyl]indol-7-yloxymethyl>-1H-tetrazole The nitrile (Example 18b part (i)) was reacted with tributyl tin azide as described in Example 5b part (ii). The crude product was dissolved in dimethylformamide and purified by RPHPLC on a C18 column eluting with 90 methanol:10 water:0.1 acetic acid. Concentration of the eluate gave a pale solid, m.p. 181°–184° C.
NMR (300 MHz, (CD$_3$)$_2$SO) δ2.57, 3.00 (two 2p, t, CH$_2$CH$_2$CO$_2$H) 5.48 (2p, s, CH$_2$O), 5.61 (2p, s, CH$_2$N), 6.55 (1p, indole 3H). MS M=530.

EXAMPLE 19

5-<1-[3-{2(E)-(Quinolin-2-yl)ethenyl}benzyl]indol-7-yloxy-methyl>-1H-tetrazole hydrochloride (alternative method)

a) 1-(3-Formylbenzyl)-7-cyanomethoxyindole i) Methyl 3-(1,3-dioxolan-2-yl)benzoate

A stirred solution of methyl 3-formylbenzoate (10.0 g., 61 mmol), ethylene glycol (5.0 ml, 91 mmol) and p-toluene sulphonic acid (10 mb) in toluene (100 ml) was refluxed under a Dean and Stark water trap for 4 hours. The cooled solution was washed with sodium bicarbonate solution, dried and evaporated to a pale oil.

ii) 3-(1,3-Dioxolan-2-yl)benzyl alcohol

A solution of methyl 3-(1,3-dioxolan-2-yl)benzoate (11.0 g., 53 mmol) in tetrahydrofuran (50 ml) was added dropwise to a stirred suspension of lithium aluminium hydride (3.2 g) in tetrahydrofuran (100 ml). The temperature rose to ca. 45° C. The mixture was stirred for a further 1 hour cooling to room temperature, then was cooled in ice whilst water (3.2 ml) 2M sodium hydroxide (6.4 ml) and more water (6.4 ml) were added dropwise. The mixture was filtered through a pad of Celite filter acid and the filtrate was evaporated to a colourless oil.

iii) 3-(1,3-Dioxolan-2-yl)benzyl bromide

Solid N-bromosuccinimide (10.4 g., 58 mmol) was added in small portions to a stirred solution of 3-(1,3-dioxolan-2-yl)benzyl alcohol (9.6 g., 53 mmol) and triphenylphosphine (16.7 g., 64 mmol) in dichloromethane (250 ml) at ca. −5° C. The yellow solution was stirred for a further 2 hours at −5° C. then added to a suspension of silica (50 g) in dichloromethane (250 ml) and triethylamine (2.5 ml). The mixture was evaporated and the residual silica was placed on the top of a silica column (250 g) and eluted with ethyl acetate-hexane (1:4) to give the product as a pale solid.

iv) 1-[3-(1,3-Dioxolan-2-yl)benzyl]-7-cyanomethoxy indole

60% Sodium hydride dispersion in mineral oil (90 mg, 2.25 mmol) was added to a stirred, cooled solution of 7-cyanomethoxyindole (Example 1a) (0.32 g., 1.86 mmol) in tetrahydrofuran (8 ml). The dark mixture was stirred for 15 minutes at room temperature then cooled again whilst a solution of 3-(1,3-dioxolan-2-yl)benzyl bromide (0.50 g., 2.06 mmol) in tetrahydrofuran (2 ml) was added. The mixture was stirred at room temperature for 20 hours then treated with glacial acetic acid (130 µl), diluted with dichloromethane, washed with water, dried and evaporated. The residue was chromatographed on silica in ethyl acetate-hexane (1:3).

v) 1-(3-Formylbenzyl)-7-cyanomethoxyindole

A solution of 1-[3-(1,3-dioxolan-2-yl)benzyl]-7-cyanomethoxyindole (50 mg., 0.15 mmol) in tetrahydrofuran (1 ml) and 2M hydrochloric acid (0.5 ml) was stirred at room temperature for 1 hour, diluted with water and extracted with ethyl acetate. The extract was dried and evaporated to a dark oil.

b) i)
1-[3-{2(E)-(Quinolin-2-yl)ethenyl}benzyl]indol-7-yloxyacetonitrile A solution of sodium bis(trimethylsilyl)amide in tetrahydrofuran (0.20 ml of M solution) was added to a stirred suspension of quinolin-2-ylmethyl-triphenylphosphonium chloride (72 mg, 0.16 mmol) in tetrahydrofuran (5 ml) under nitrogen. The yellow solution was stirred for 30 minutes at room temperature then cooled to −70° C. A solution of 1-(3-formylbenzyl)-7-cyanomethoxyindole (43 mg, 0.15 mmol) in tetrahydrofuran (1 ml) was added and the mixture was stirred for a further 1 hour at −70° C., warmed to room temperature and evaporated. The residue was chromatographed on silica in ethyl acetate-hexane (1:2) to give a pale solid (38 mg).

ii)

5-<1-[3-{2(E)-(Quinolin-2-yl)ethenyl}benzyl]indole-7-yloxymethyl>-1H-tetrazole hydrochloride The nitrile (Example 19b part i) was converted to the tetrazole product by the method described in Example 1c part (ii) giving an identical product.

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 or 100 ul equivalent to 0.5–1 mg active ingredient.

EXAMPLE 20

5-<1-[α-{3-(1H-Tetrazol-5-yl)phenyl}-3-{2(E)-(quinolin-2-yl)ethenyl}benzyl]indol-7-yloxymethyl>-1H-tetrazole a)

3-[α-Chloro-3-{2-(E)-(quinolin-2-yl)ethenyl}benzyl]-benzonitrile i)

3-[α-Hydroxy-3-{2-(E)-(quinolin-2-yl)ethenyl}benzyl]-benzonitrile 2.5M n-Butyl lithium solution in hexane (2.6 ml) was added dropwise to a stirred solution of 3-bromobenzonitrile (1.2 g, 6.56 mmol) in tetrahydrofuran (20 ml) and ether (20 ml) at −100° to −110° C. under nitrogen. The yellow solution was stirred at −100° C. for 5 minutes, then a solution of 3-[2(E)-(quinolin-2-yl)ethenyl]-benzaldehyde (1.7 g, 6.56 mmol) in tetrahydrofuran (7 ml) was added. The dark brown solution was allowed to warm to room temperature, poured onto saturated ammonium chloride solution and extracted with ethyl acetate. The extract was dried and evaporated and the residue was chromatographed on silica in ethyl acetate-hexane (1:2) to give a pale yellow solid.

ii)

3-[α-Chloro-3-{2(E)-(quinolin-2-yl)ethenyl}benzyl]-benzonitrile

A suspension of the 3-[α-hydroxy-3-{2(E)-(quinolin-2-yl)ethenyl}benzyl]benzonitrile (1.4 g, 3.87 mmol) in dichloromethane (75 ml) was stirred with concentrated hydrochloric acid (75 ml) for 3 hours, diluted with water and neutralised with saturated sodium bicarbonate solution. The aqueous layer was extracted with further dichloromethane and the combined solvent was dried and evaporated to a pale solid.

b) i)

1-[-α-(3-Cyanophenyl)-3-{2(E)-(quinolin-2-yl)ethenyl}benzyl]indol-7-yloxyacetonitrile This compound was prepared by the method described in Example 16b, part i (without RP-HPLC).

ii)

5-<1-[α-{3-(1H-Tetrazol-5-yl)phenyl}-3-{2(E)-quinolin-2-yl)ethenyl}benzyl]indol-7-yloxymethyl>-1H-tetrazole The dinitrile was reacted with tributyl tin azide as described in Example 5b part ii and the crude product was purified by RP-HPLC on a C18 column eluting with 80 methanol:20 water:0.1 acetic acid. Evaporation of the eluate gave a yellow solid m.p. ca. 200° C. (dec.).

NMR (300 MHz, (CD$_3$)$_2$SO) δ5.41 (2p, s, OCH$_2$), 6.52 (1p, indole 3H), 7.39, 7.76 (two 1p, d, —CH═CH—).

EXAMPLE 21

5-<1-{3-[2(E)-(7-Chloroquinolin-2-yl)ethenyl]-α-phenyl-benzyl}indol-7-yloxymethyl>-1H-tetrazole This compound was prepared from 7-cyanomethoxyindole (Example 1a) and 3-[2(E)-(7-chloroquinolin-2-yl)ethenyl]-α-phenyl-benzyl chloride (prepared from 3-[2(E)-(7-chloroquinolin-2-yl)ethenyl]benzaldehyde by the methods described in Example 20a part i and Example 14b) according to the procedures described for Example 16b.

$^1$H-NMR (300 MHz, DMSO-d$^6$) δ5.44 (2H, s, OCH$_2$), 6.50 (1H, d indole-3H), 7.37/7.76 (2×1H, d, CH═CH), 7.74 (1H, s, Ar$_2$CHN).

EXAMPLE 22

5-<1-{α-(3-Chlorophenyl)-3-[2(E)-(7-chloroquinolin-2-yl)ethenyl]benzyl}indol-7-yloxymethyl>-1H-tetrazole This compound was prepared in a similar fashion to that described in Example 21.

$^1$H-NMR (300 MHz, DMSO-d$^6$) δ5.47/5.49 (2H, OCH$_2$), 6.52 (1H, d, indole-3H), 7.40/7.78 (2×1H, d, CH═CH), 7.75 (1H, s, Ar$_2$CHN).

EXAMPLE 23

5-<1-{3-[2(E)-(7-Chloroquinolin-2-yl)ethenyl]-α-(3-trifluoromethylphenyl)benzyl}indol-7-yloxymethyl>-1H-tetrazole This compound was prepared in a similar fashion to that described for Example 21.

$^1$H-NMR (300 MHz, DMSO-d$^6$) δ5.35 (2H, s, OCH$_2$), 6.52 (1H, d, indole-3H), 7.43/7.80 (2×1H, d, CH═CH), 7.60 (1H, S, Ar$_2$CHN).

EXAMPLE 24

5-<1-{α-(4-Chlorophenyl)-3-[2(E)-(7-chloroquinolin-2-yl)ethenyl]benzyl}indol-7-yloxymethyl>-1H-tetrazole This compound was prepared in a similar fashion to that described for Example 21.

$^1$H-NMR (300 MHz, DMSO-d$^6$) δ5.35 (2H, s, OCH$_2$), 6.48 (1H, d, indole-3H), 7.46/7.80 (2×1H, d, CH═CH), 7.82 (1H, s, Ar$_2$CHN).

EXAMPLE 25

5-<1-{3-[2(E)-(7-Chloroquinolin-2-yl)ethenyl]-α-(3-methoxyphenyl)benzyl}indol-7-yloxymethyl>1H-tetrazole This compound was prepared in a similar fashion to that described for Example 21.

$^1$H-NMR (300 MHz, DMSO-d$^6$) δ5.47 (2H, s, OCH$_2$), 6.50 (1H, d, indole-3H), 7.35/7.76 (2×1H, d, CH═CH), 7.69 (1H, s, Ar$_2$CHN).

EXAMPLE 26

5-<1-{3-[2(E)-(7-Chloroquinolin-2-yl)ethenyl]-α-(4-methylphenyl)benzyl}indol-7-yloxymethyl>-1H-tetrazole This compound was prepared in a similar fashion to that described for Example 21.

$^1$H-NMR (300 MHz, DMSO-d$^6$) δ5.45 (2H, s, OCH$_2$), 6.49 (1H, d, indole-3H), 7.35/7.75 (2×1H, d, CH=CH), 7.66 (1H, s, Ar$_2$CHN).

EXAMPLE 27

5-<1-[α-{4-(1H-Tetrazol-5-yl)phenyl}-3-{2(E)-(quinolin-2-yl)ethenyl}benzyl]indol-7-yloxymethyl>-1H-tetrazole a)
4-[α-Chloro-3-{2(E)-(quinolin-2-yl)ethenyl}benzyl]-benzonitrile

This compound was prepared by the methods described in Example 20a and purified by chromatography on silica.

b) i)
1-[α-(4-Cyanophenyl)-3-{2(E)-(quinolin-2-yl)ethenyl}benzyl]indol-7-yloxyacetonitrile This compound was prepared by the method described in Example 16b part i.

ii)
5-<1-[α-{4-(1H-Tetrazol-5-yl)phenyl}-3-{2(E)-(quinolin-2-yl)ethenyl}benzyl]indol-7-yloxymethyl>1H-tetrazole This compound was prepared by the method described in Example 14c part ii (using more tributyl tin azide). The crude product was purified by washing with ether, solution in methanol and 0.2M sodium hydroxide, and precipitation with aqueous acetic acid.

NMR (300 MHz, (CD$_3$)$_2$SO) δ6.54 (1p indole 3H).

EXAMPLE 28

3-{1-<3-[2(E)-(7-Chloroquinolin-2-yl)ethenyl]benzyl>indol-7-yl}propanoic acid a)
3-{1-<3-[2(E)-(7-Chloroquinolin-2-yl)ethenyl]benzyl>indol-7-yl}propanoic acid methyl ester A solution of 7-(2-cyanoethyl)-1-[3-{2(E)-(7-chloroquinolin-2-yl)ethenyl}benzyl]indole (Example 14c) (112 mg, 0.25 mmol) in dichloromethane (5 ml) and methanolic hydrogen chloride solution (5 ml) was heated under reflux for 24 hours adding further methanolic hydrogen chloride (5 ml) after 16 hours. The solution was poured onto saturated sodium bicarbonate solution and extracted with dichloromethane. The extract was dried and evaporated and the residue was chromatographed on silica in ethyl acetate-hexane (1:3) to give a pale solid.

b)
3-{1-<3-[2(E)-(7-Chloroquinolin-2-yl)ethenyl]benzyl>indol-7-yl}propanoic acid A solution of the methyl ester (Example 28a) (88 mg, 0.18 mmol) in tetrahydrofuran (5 ml) was stirred with M lithium hydroxide solution (5 ml) for 16 hours. The solution was acidified with dilute acetic acid and the precipitate was washed with water (5 ml), dimethyl formamide (0.5 ml) and methanol (2 ml), m.p. 241° C.

NMR (300 MHz, (CD$_3$)$_2$SO) δ2.45, 3.06 (two 2p, t, CH$_2$CH$_2$CO$_2$H), 5.67 (2p, s, CH$_2$N), 6.58 (1p, indole 3H), 7.37, 7.76 (two 1p, d, —CH=CH—). MS M=466/468.

EXAMPLE 29

5-<1-{3-[2(E)-(7-Chloroquinolin-2-yl)ethenyl]benzyl}-indol-6-yl methyl>-1H-tetrazole a) 6-Formyl indole i) 6-Hydroxymethyl indole

To a suspension of lithium aluminium hydride (6.18 g, 2 mol. eq.) in dry THF (350 ml) under nitrogen was added dropwise a solution of methyl indole-6-carboxylate (14.2 g, 81.1 mmol) in dry THF (350 ml) and stirred for 4 hours. The gelatinous suspension was quenched with 2N hydrochloric acid, extracted into diethyl ether, and the combined organic extracts dried, filtered and evaporated in vacuo to yield a yellow oil.

ii) 6-Formyl indole

To a solution of 6-hydroxymethyl indole (4.9 g, 33.3 mmol) in dry dichloromethane (200 ml) was added a solution of pyridinium dichromate (15.97 g, 42.5 mmol) in dry dichloromethane (100 ml) and the suspension stirred at room temperature for 5 hours. The suspension was diluted with diethyl ether and filtered through a pad of silica to give an orange solution, which was evaporated in vacuo. The crude solid was purified by flash chromatography on silica, eluting with 50% diethyl ether in hexane, to yield a pale orange solid. Recrystallisation from diethyl ether/40°–60° C. petrol gave a pale orange crystalline solid, m.p. 126°–128° C.

b)
1-{3-[2(E)-(7-Chloroquinolin-2-yl)ethenyl]benzyl}indol-6-yl-acetonitrile i)
1-{3-[2(E)-(7-Chloroquinolin-2-yl)ethenyl]benzyl}-6-formyl-indole

To a solution of 6-formyl indole (Example 29a) (0.63 g, 4.3 mmol) in dry DMF (20 ml) was added sodium hydride (60% dispersion in oil) (0.22 g, 5.5 mmol) portionwise over 5 minutes with stirring. The reaction mixture was stirred for a further 20 minutes, then solid 3-[2(E)-(7-chloroquinolin-2-yl)ethenyl]benzyl chloride (Example 14b) (1.7 g, 5.4 mmol) was added portionwise over 5 minutes, and the reaction mixture left to stir for 18 hours. The reaction was quenched with water, extracted into ethyl acetate, the combined organic extracts washed with water, then brine, dried, filtered and evaporated in vacuo. The crude solid was purified by flash chromatography on silica, eluting with 30% diethyl ether in hexane to give a pale yellow solid.

ii)
1-{3-[2(E)-(7-Chloroquinolin-2-yl)ethenyl]benzyl}indol-6-yl-acetonitrile A solution of toluene sulphonyl methyl isocyanide (0.65 g, 3.3 mmol) in dry dimethoxyethane (10 ml) was added dropwise to a stirred suspension of potassium t-butoxide (0.75 g, 6.7 mmol) in dimethoxyethane (10 ml) cooled below −30° C. under nitrogen.

A solution of the 6-formyl indole (Example 29b part i) (1.31 g, 3.1 mmol) in dimethoxyethane (10 ml) was then added dropwise at −50° to −60° C. After 1 hour methanol (20 ml) was added to the cold solution, which was then heated at reflux for 15 minutes. The cooled solution was quenched with water (50 ml) containing acetic acid (1 ml), and extracted with dichloromethane, dried, filtered and evaporated in vacuo. The crude product was purified by flash chromatography on silica, eluting with 50% diethyl ether in hexane to yield a pale yellow solid.

c)
5-<1-{3-[2(E)-(7-Chloroquinolin-2-yl)ethenyl]benzyl}-indol-6-yl methyl>-1H-tetrazole To a solution of the indole acetonitrile (Example 29b) (0.8 g, 1.8 mmol) in dry THF (5 ml) was added tributyl tin azide (0.67 g, 2.1 mmol) and the reaction mixture heated at 150° C. with stirring for 75 minutes, allowing the solvent to distill off rapidly. The cooled gum was dissolved in dichloromethane and purified by flash chromatography on silica, eluting with dichloromethane/hexane/methanol (49:49:2). Recrystallisation from dichloromethane/diethyl ether gave a yellow solid, m.p. 179°–181° C.

$^1$H-NMR (300 MHz, DMSO-d$^6$) δ4.35 (2H, s, CH$_2$Tet), 5.45 (2H, s, CH$_2$N) 6.50 (1H, d, Indole-3H), 7.44/7.81 (2×1H, d, CH=CH).

EXAMPLE 30

5-<2-[1-{3-[2(E)-(7-Chloroquinolin-2-yl)ethenyl]benzyl}indol-6-yl ethyl>-1H-tetrazole a) 6-Cyanoethyl indole This compound was prepared from 6-formyl indole (Example 29a) using similar methods to those described in Examples 10a, parts v and vi. The product was recrystallised from ether/hexane to give a colourless crystalline solid.

b)
5-<1-{3-[2(E)-(7-Chloroquinolin-2-yl)ethenyl]benzyl}indol-6-yl ethyl>-1H-tetrazole i)
3-<1-{3-[2(E)-(7-Chloroquinolin-2-yl)ethenyl]benzyl}-indol-6-yl>propionitrile To a solution of 6-cyanoethyl indole (Example 30a) (0.76 g, 4.5 mmol) in dry DMF (25 ml) at room temperature was added sodium hydride (60% dispersion in oil) (0.22 g, 5.5 mmol) portionwise over 10 minutes. The suspension was stirred for a further 20 minutes, then solid 3-[2(E)-(7-chloroquinolin-2-yl)ethenyl]benzyl chloride (Example 14b) (1.75 g, 5.6 mmol) was added over 5 minutes and the reaction mixture allowed to stir for 18 hours at room temperature. The solution was diluted with water, extracted into ethyl acetate, and the combined organic extracts washed with water, then brine, dried, filtered and evaporated in vacuo. The crude oil was purified by flash chromatography on silica, eluting with 60% diethyl ether in hexane to yield a pale yellow solid. Recrystallisation from dichloromethane/ether gave a yellow crystalline solid m.p. 131°–137° C.

ii)
5-<1-{3-[2(E)-(7-Chloroquinolin-2-yl)ethenyl]benzyl}indol-6-yl ethyl>-1H-tetrazole This compound was prepared from the nitrile (Example 30b), part i) using the method described for Example 30c. Recrystallisation from dichloromethane/diethyl ether gave a yellow crystalline solid, m.p. 175°–177° C.

$^1$H-NMR (300 MHz, DMSO-d$^6$) δ3.13/3.22 (2×2H, t, (CH$_2$)$_2$ Tet), 5.43 (2H, s, NCH$_2$), 6.45 (1H, d, indole-3H), 6.92 (1H, dd, indole-5H), 7.45/7.83 (2×1H, d, CH=CH).

EXAMPLE 31

5-<1-[1-{3-[2(E)-(7-Chloroquinolin-2-yl)ethenyl benzyl}indol-6-yl]ethyl>-1H-tetrazole a)
6-(1-Cyanoethyl)-1-{3-{2(E)-(7-chloroquinolin-2-yl)ethenyl}benzyl]indole A solution of 6-(cyanomethyl)-1-[3-{2(E)-(7-chloroquinolin-2-yl)ethenyl}benzyl]indole (Example 29b) (180 mg, 0.41 mmol), methyl iodide (77 μl, 1.24 mmol) and benzyl-triethyl-ammonium chloride (94 mg, 0.41 mmol) in dichloromethane (3 ml) was stirred with a solution of sodium hydroxide (1.5 g) in water (1.5 ml) heating under reflux for 2 hours. The mixture was diluted with dichloromethane and water and the aqueous layer was extracted with further dichloromethane. The combined solvent layer was dried and evaporated and the residue was chromatographed on silica in ethyl acetate-hexane (1:3). The resulting crude product was further purified by RP-HPLC on a C18 column (eluting with 85 methanol:15 water:0.1 acetic acid) followed by crystallisation from methanol-water.

b)
5-<1-[1-{3-[2(E)-(7-Chloroquinolin-2-yl)ethenyl]benzyl}indol-6-yl]ethyl> 1H-tetrazole This compound was prepared as its crude hydrochloride salt by the method described in Example 14c part ii and purified by RP-HPLC on a C18 column (eluting with 85 methanol:15 water:0.1 acetic acid). Evaporation of the eluate gave a yellow solid, m.p. ca 150° (dec).

NMR (300 MHz, (CD$_3$)$_2$SO) δ1.70 (3p, d, CH$_3$CH), 4.60 (1p, d, CH Me), 5.64 (2p, s, CH$_2$N), 6.47 (1p, indole 3H), 7.44, 7.81 (two 1p, d, —CH=CH—). MS M=491/493.

EXAMPLE 32

5-<2-{1-[3-{2(E)-(7-Chloroquinolin-2-yl)ethenyl}benzyl]-indol-7-yl}-1-methyl ethyl>-1H-tetrazole a) 7-(2-Cyano-1-methyl ethyl) indole i) 7-Acetyl indole This compound was prepared from 7-bromoindole using the method described for Example 14a part i, quenching the dianion so formed with dimethyl acetamide instead of dimethyl formamide.

ii) 7-(2-Cyano-1-methyl ethenyl) indole

This compound was prepared from 7-acetyl indole using the method described for Example 10a part v, m.p. 88°–90° C.

iii) 7-(2-Cyano-1-methyl ethyl) indole

This compound was prepared from the unsaturated compound (Example 32a part ii) by hydrogenation, according to the method described for Example 10a part vi.

b)
5-<2-{1-[3-{2(E)-(7-Chloroquinolin-2-yl)ethenyl}benzyl]-indol-7-yl}-1-methyl ethyl>-1H-tetrazole This compound was prepared from 7-(2-cyano-1-methyl-ethyl)indole (Example 32a) and 3-[2(E)-(7- chloroquinolin-2-yl)ethenyl]benzyl chloride (Example 14b) according to the methods described for Example 30b, m.p. 175°–178° C.

EXAMPLE 33

5-<1-{3-[2(E)-(7-Chloroquinolin-2-yl)ethenyl]benzyl}-3-methyl-indol-7-yl ethyl>1H-tetrazole a) 7-Formyl-3-methylindole i) 7-Bromo-3-methylindole

Magnesium turnings (1.45 g) in dry THF (10 ml) were stirred at room temperature under nitrogen and an iodine crystal added, followed by a few milliliters of a solution of 1-bromo-1-propene (7.25 g, 0.06 mole) in dry THF (50 ml). After warming to initiate the reaction, the remaining bromopropene solution was added dropwise at a rate to maintain reflux. After addition, the reaction was heated at reflux for a further hour, cooled and added rapidly to a stirred solution of 2-bromonitrobenzene (4.04 g, 0.02 mole) in dry THF (70 ml) at −40° C. under nitrogen. The reaction mixture was stirred for a further 30 minutes at −40° C., then was quenched with saturated aqueous ammonium chloride and extracted into diethyl ether. The combined organic extracts were washed with water, dried, filtered and evaporated in vacuo. The crude product was purified by flash chromatography on silica, eluting with 25% diethyl ether in hexane, to yield a yellow-orange oil.

ii) 7-Formyl-3-methylindole

This compound was prepared from the bromo indole (Example 33a part i) (8.8 g) using the method described for Example 14a, part i), and purified by flash chromatography on silica eluting with 30% diethyl ether in hexane to give a yellow solid (4.73 g). Recrystallisation from 40°–60° C. petrol gave a yellow crystalline solid, m.p. 77°–79° C.

iii) 7-[2(E)-Cyanoethenyl]-3-methyl indole

This compound was prepared from 7-formyl-3-methylindole by the method described in Example 10a part v. The crude product was recrystallised from toluene to give a yellow crystalline solid, m.p. 225°–227° C.

iv) 7-Cyanoethyl-3-methylindole

This compound was prepared from 7-[2(E)-cyanoethenyl]-3-methylindole by the method described in Example 10a part vi. The crude product was recrystallised from diethyl ether/hexane to give colourless crystals, m.p. 146°–148° C.

b) 5-<1-{3-[2(E)-(7-Chloroquinolin-2-yl)ethenyl]benzyl}-3-methyl indol-7-yl ethyl>1H-tetrazole This compound was prepared from 7-cyanoethyl-3-methyl-indole (Example 33a) and 3-[2(E)-(7-chloroquinolin-2-yl)ethenyl]-benzyl chloride (Example 14b) according to the methods described for Example 30b, m.p. 226°–229° C.

$^1$H-NMR (300 MHz, DMSO-d$^6$) δ2.30 (3H, s, 3-Me), 3.09/3.26 (2×2H, t, (CH$_2$)$_2$Tet), 5.62 (2H, s, NCH$_2$), 7.43/7.74 (2×1H, d, CH=CH).

EXAMPLE 34

5-<1-{3-[2(E)-(7-Chloroquinolin-2-yl)ethenyl]-α-[3-(1H-tetrazol-5-yl)propyl]benzyl}indol-7-yl oxymethyl>-1H-tetrazole a) 7-Cyanomethoxy indole i) 2-Benzhydryloxy nitrobenzene

2-Nitrophenol (11.0 g, 79 mmole), anhydrous potassium carbonate (17.6 g, 127.4 mmole) and benzhydryl bromide (19.6 g, 79 mmol) in acetone (220 ml) were refluxed under nitrogen for 5 hours. The mixture was cooled, filtered and evaporated in vacuo. The residue was triturated with diethyl ether, filtered and evaporated. Trituration with 60°–80° C. petroleum ether yielded a brown solid.

ii) 7-Benzhydryloxy indole

To a stirred solution of the protected nitrophenol (3.05 g, 10 mmol) (Example 34a part i) in dry THF (100 ml) at −40° C. under nitrogen was added 1M vinyl magnesium bromide in the THF (35 ml) over 5 minutes. After stirring for a further three quarters of an hour at −40° C., the reaction mixture was poured into aqueous ammonium chloride and extracted into diethyl ether. The combined organic extracts were dried, filtered and evaporated in vacuo. The product was purified by column chromatography on silica, eluting with 12.5% ethyl acetate in hexane, to give a pale yellow solid.

iii) 7-Cyanomethoxy indole

The protected 7-substituted indole (Example 34a part ii) (0.53 g, 1.75 mmol) in methanol (10 ml) and toluene (10 ml) was hydrogenated in a Parr apparatus at 50 p.s.i. for 1 hour in the presence of Pearlman's catalyst (0.33 g). The reaction mixture was filtered through Celite and the filtrate evaporated in vacuo. The crude 7-hydroxy indole was taken up in methyl ethyl ketone (20 ml), and bromoacetonitrile (0.65 g, 5.25 mmol) and anhydrous potassium carbonate (0.6 g, 4.35 mmol) added. The mixture was refluxed under nitrogen for 1 hour, cooled, poured into 2.5M hydrochloric acid/ice and extracted into dichloromethane. The organic phase was washed with water, dried, filtered and evaporated in vacuo.

The product was purified by column chromatography on silica, eluting with 20% ethyl acetate in hexane to yield a bronze coloured solid.

b) 5-Chloro-5-{3-[2(E)-(7chloroquinolin-2-yl)ethenyl]-phenyl}pentane nitrile i) 5-Hydroxy-5-{3-[2(E)-(7-chloroquinolin-2-yl)ethenyl]-phenyl pentane nitrile A suspension of zinc dust (0.85 g, 13 mmol) in dry THF (1 ml) containing dibromoethane (0.095 g, 0.5 mmol) was heated at 65° C. for 1 minute with stirring. After cooling to room temperature, trimethyl silyl chloride (50 μl, 0.4 mmol) was added and the reaction stirred for 15 minutes. 4-Iodo-butyronitrile (2.44 g, 12.5 mmol) in dry THF (5 ml) was added dropwise over 15 minutes and the reaction mixture stirred for 18 hours at 40° C. The resultant zincate was cooled to room temperature.

3-[2(E)-(7-Chloroquinolin-2-yl)ethenyl]benzaldehyde (Example 6a, part i) (1.82 g, 6.2 mmol) in dry THF (10 ml) was added to the zincate solution, and the resultant mixture cooled to 0° C. 1M Titanium tetrachloride in dichloromethane (6.2 ml, 6.2 mmol) was added dropwise with stirring over 5 minutes, the dark solution stirred for a further half hour at 0° C., then for 3 hours at room temperature.

The reaction mixture was diluted with 20% methanol in chloroform and washed with aqueous sodium hydroxide, then water. The organic extracts were dried, filtered and evaporated in vacuo. The crude product was purified by flash chromatography on silica, eluting with 25–50% ethyl acetate in hexane to yield a pale gum. Crystallisation from diethyl ether gave colourless crystals.

ii)
5-Chloro-5-{3-[2(E)-(7-chloroquinolin-2-yl)ethenyl]-phenyl}pentane nitrile

A solution of the alcohol (Example 34b, part i) (0.90 g, 2.5 mmol) in dichloroethane (50 ml) was cooled to 0° C. and stirred as thionyl chloride (0.22 ml, 3 mmol) was added over 2 minutes. The reaction was stirred for a further half hour at 0° C., then 3 hours at room temperature. The mixture was diluted with dichloromethane and washed with aqueous sodium bicarbonate, then water, dried, filtered and evaporated in vacuo.

The crude sample, containing approximately 10% of the corresponding styrene by n.m.r., was used in the next step without further purification.

c)
5-<1-{3-[2(E)-(7-Chloroquinolin-2-yl)ethenyl]-α-[3-(1H-tetrazol-5-yl)propyl]benzyl}indol-7-yl oxymethyl>-1H-tetrazole i)
2-<1-{3-[2(E)-(7-Chloroquinolin-2-yl)ethenyl]-α-[3-cyanopropyl]benzyl}indol-7-yl oxy>acetonitrile 7-Cyanomethyloxy indole (Example 34a) (0.33 g, 1.9 mmol) was dissolved in dry DMF (10 ml) and stirred as sodium hydride (0.084 g, 2.1 mmole) (60% dispersion in mineral oil) was added in portions over 5 minutes. The reaction mixture was stirred at room temperature for half an hour, then the chloride (Example 34b) (0.88 g, 2.3 mmole) in dry THF (2 ml) added. The stirred reaction mixture was heated at 55° C. for 18 hours, then cooled, poured into water and extracted into ethyl acetate. The organic extracts were washed twice with water, then brine, dried, filtered and evaporated in vacuo.

The crude product was purified by flash chromatography on silica, eluting with 25–40% ethyl acetate in hexane, to yield required product and recovered 7-cyanomethyloxyindole ii)
5-<1-{3-[2(E)-(7-Chloroquinolin-2-yl)ethenyl]-α-[3-(1H-tetrazole-5-yl)propyl]benzyl}indol-7-yl oxymethyl>-1H-tetrazole The dinitrile (Example 34c, part i) (0.1 g, 0.19 mmol) and tributyl tin azide (0.192 g, 0.58 mmol) were dissolved in dimethoxethane (1.5 ml), and heated at 120° C. for 8 hours, allowing the solvent to evaporate off. The resultant gum was partially cooled, taken up in dimethoxyethane and acidified with acetic acid. The product was purified by flash chromatography on silica, eluting with 0–10% methanol in dichloromethane. The resulting yellow solid was triturated with dichloromethane and filtered off to give the product.

$^{1}$H-NMR (300 MHz, DMSO-d$^{6}$) δ1.69 (2H, m), 2.25/2.50 (2H, m), 2.96 (2H, t), 5.60 (2H, s), 6.30 (1H, t), 6.55 (1H, d), 6.82 (1H, d), 6.93 (1H, t), 7.12 (1H, d), 7.19 (1H, d), 7.27 (1H, t), 7.40 (1H, d), 7.54 (1H, d), 7.60 (1H, d), 7.61 (1H, dd), 7.74 (1H, d), 7.76 (1H, d), 7.92 (1H, d), 8.01 (1H, d), 8.03 (1H, d), 8.42 (1H, d). MS [M+H]=603/605.

EXAMPLE 35

5-<1-{3-[2(E)-(7-Chloroquinolin-2-yl)ethenyl]-α-methylbenzyl}indol-7-yl oxymethyl>-1H-tetrazole a)
1-Chloro-1-{3-[2(E)-(7-chloroquinolin-2-yl)ethenyl]-phenyl}ethane i)
1-{3-[2(E)-(7-Chloroquinolin-2-yl)ethenyl]phenyl}ethanol 3-[2(E)-(7-Chloroquinolin-2-yl)ethenyl]benzaldehyde (Example 6a part i) (2.44 g, 8.3 mmol) in dry THF (75 ml) was cooled in an ice bath under nitrogen and stirred as 1M methyl magnesium iodide in diethyl ether (9.9 ml) was added over 5 minutes. The reaction was stirred at 0° C. for half an hour, warmed to room temperature and quenched with water. The mixture was extracted into ethyl acetate, the combined organic extracts dried, filtered and evaporated in vacuo.

Purification by flash chromatography on silica, eluting with 0–25% ethyl acetate in chloroform, yielded a colourless crystalline solid.

ii)
1-Chloro-1-{3-[2(E)-(7-chloroquinolin-2-yl)ethenyl]-phenyl}ethane

The alcohol (Example 35a part i) (1.15 g, 3.55 mmol) in dichloroethane (25 ml) was cooled in an ice bath, and thionyl chloride (0.32 ml, 4.4 mmol) was added to the stirred suspension over 2 minutes. The reaction was further stirred at 0° C. for 15 minutes, then at room temperature for 1 hour. The mixture was washed with aqueous potassium carbonate, then water, dried, filtered and evaporated in vacuo.

Crystallisation from ethyl acetate/hexane allowed removal of the styrene contaminant. The mother liquors containing the required product were evaporated in vacuo and used in the next step without further purification.

b)
5-<1-{3-[2(E)-(7-Chloroquinolin-2-yl)ethenyl]-α-methylbenzyl}indol-7-yl oxymethyl>-1H-tetrazole i)
2-<1-{3-[2(E)-(7-Chloroquinolin-2-yl)ethenyl]-α-methyl-benzyl}indol-7-yl oxy>acetonitrile The benzyl chloride (Example 35a) (0.79 g, 2.4 mmole) was reacted with 7-cyanomethyloxyindole (Example 25a) (0.34 g, 2 mmol) as described in Example 26c part i to yield the required product.

ii)
5-<1-{3-[2(E)-(7-Chloroquinolin-2-yl)ethenyl]-α-methyl-benzyl}indol-7-yl oxymethyl>-1H-tetrazole The nitrile (Example 35b part i) (0.25 g, 0.54 mmol) was reacted with tributyl tin azide (0.27 g, 0.81 mmol) as described in Example 25c part ii. On acidification with acetic acid, the product crystallised out from the dimethoxyethane solution to yield a yellow microcrystalline solid, m.p. 237°–238° C.

¹H-NMR (300 MHz, DMSO-d⁶) δ1.86 (3H, d), 5.49/5.57 (2×1H, d), 6.45 (1H, q), 6.54 (1H, d), 6.80 (1H, d), 6.93 (1H, t), 6.97 (1H, d), 7.20 (1H, d), 7.26 (1H, t), 7.35 (1H, d), 7.40 (1H, bs), 7.56 (1H, d), 7.59 (1H, dd), 7.68 (1H, d), 7.71 (1H, d), 7.91 (1H, d), 8.01 (1H, d), 8.02 (1H, s), 8.41 (1H, d). MS [M+H]=507/509.

EXAMPLE 36

5-<1-{3-[2(E)-(7-Chloroquinolin-2-yl)ethenyl]-α-ethylbenzyl}indol-7-yloxymethyl>-1H-tetrazole This compound was synthesised according to the methods described for Example 35, m.p. 161°–162° C.

¹H-NMR (300 MHz, DMSO-d⁶) δ0.84 (3H, t), 2.21/2.34 (2H, m), 5.53 (2H, s), 6.21 (1H, t), 6.52 (1H, d), 6.85 (1H, d), 6.92 (1H, t), 7.16 (1H, d), 7.17 (1H, d), 7.28 (1H, t), 7.42 (1H, d), 7.56 (1H, s), 7.57 (1H, d), 7.59 (1H, d), 7.71 (1H, d), 7.76 (1H, d), 7.90 (1H, d), 8.01 (1H, d), 8.02 (1H, s), 8.42 (1H, d). MS [M+H]=521/523.

EXAMPLE 37

5-<1-{3-[2(E)-(2-Pyridyl)ethenyl]benzyl}indol-7-yl ethyl>-1H-tetrazole a) 7-(2-Cyanoethyl) indole i) 7-Formyl indole

A mixture of 2-nitrobenzaldehyde (70 g, 0.46 mol), n-butanol (100 g, 1.35 mol) and 4-toluene sulphonic acid (0.5 g) in toluene (700 ml) was heated at reflux for 4 hours with water removal via a Dean-Stark apparatus. On cooling, the solvent was removed in vacuo and the residue taken up in diethyl ether. The solution was washed with aqueous sodium bicarbonate, then aqueous sodium metabisulphite, dried, filtered and evaporated in vacuo to give the crude dibutyl acetal.

The acetal was taken up in dry THF (2 l) and cooled to −65° C. under nitrogen. 1M Vinyl magnesium bromide in THF (1400 ml) was added rapidly over about 10 minutes, maintaining the temperature below −40° C. After stirring for 15 minutes, a further portion of 1M vinyl magnesium bromide (200 ml) was added and stirred for 25 minute. The reaction mixture was quenched with saturated aqueous ammonium chloride and extracted into diethyl ether. The combined organic extracts were dried, filtered, and evaporated in vacuo to an oil.

This oil was immediately treated with 0.5N hydrochloric acid (100 ml) in THF (800 ml), and stirred for 15 minutes under nitrogen. The mixture was then quenched with aqueous sodium bicarbonate and extracted with diethyl ether. The combined organic extracts were washed with brine, dried, filtered and evaporated in vacuo. The residue was taken up in hexane (3–4 volumes) and filtered through a pad of silica (300 g), pre-wetted with 20% ethyl acetate in hexane. The silica was further eluted with 20% ethyl acetate in hexane to yield the crude product on evaporation, as a yellow solid. This was recrystallised from 80°–100° C. petrol.

ii) 7-[2(E)-Cyanoethenyl] indole

7-Formyl indole (Example 37a part i) was reacted as in Example 10a part v to yield the cyanoethenyl indole.

iii) 7-(2-Cyanoethyl) indole

The cyanoethenyl indole (Example 37a part ii) was reacted as in Example 10a part vi to yield the cyanoethyl indole.

b) 3-[2(E)-(2-Pyridyl)ethenyl]benzyl chloride i) 2-Picolyl triphenyl phosphonium chloride

2-Picolyl chloride (7.4 g, 58 mmol) (from the hydrochloride) and triphenyl phosphine (16.7 g, 64 mmol) in toluene (100 ml) were heated at reflux for 18 hours. The reaction mixture was cooled in an ice-bath, the precipitated product filtered off and washed with toluene to yield the dried product.

ii) Methyl 3-[2(E)-(2-pyridyl)ethenyl]benzoate

The phosphonium salt (11.3 g, 29 mmol) (Example 37b part i) was dissolved in dry THF (200 ml) and cooled to −70° C. under nitrogen. 2.5M n-butyl lithium in hexane (11.6 ml, 29 mmol) was added over 15 minutes. and the reaction mixture stirred at −70° C. for a further half an hour. Methyl 3-formyl benzoate (4.32 g, 26.3 mmol) in dry THF (50 ml) was added over 10 minutes and after stirring at −70° C. for half an hour, the reaction mixture was stirred for 18 hours at room temperature. The mixture was poured into water and extracted into diethyl ether, washed with water, dried, filtered and evaporated in vacuo.

The crude product was purified by flash chromatography on silica, eluting with 40–60% diethyl ether in 60°–80° C. petrol, to yield a mixture of the trans and cis isomers. Recrystallisation from diethyl ether/40–60% petrol yielded the pure trans product.

iii) 3-[2(E)-(2-Pyridyl)ethenyl]benzyl alcohol

The methyl benzoate (Example 37b part ii) (2.25 g, 9.4 mmol) was dissolved in dry toluene (60 ml) and cooled to −70° C. under nitrogen. 1M DIBAL in dichloromethane (18.8 ml, 18.8 mmol) was added over 15 minutes and the reaction mixture allowed to warm up to −30° C. for 30 minutes. The reaction was quenched by careful addition of methanol (8 ml), then water, and after filtration through Celite the organic phase was evaporated in vacuo.

Purification by flash chromatography on silica, eluting with diethyl ether, yielded a pale oil.

iv) 3-[2(E)-(2-Pyridyl)ethye yl]benzyl chloride hydrochloride

The benzyl alcohol (Example 37b part iii) (0.83 g, 3.9 mmol) was dissolved in dichloromethane (35 ml) and cooled in an ice-bath. Thionyl chloride (1.3 g, 11 mmol) was added over 10 minutes and the reaction mixture allowed to warm to room temperature. After stirring for 18 hours, the solvent was removed in vacuo to yield crude product which was used in the next step without purification.

c) 5-<1-{3-[2(E)-(2-Pyridyl)ethenyl]benzyl}indol-7-yl ethyl>-1H-tetrazole i) 3-<1-{3-[2(E)-(2-Pyridyl)ethenyl]benzyl}indol-7-yl>propionitrile 7-(2-Cyanoethyl) indole (0.57 g, 3.35 mmol) (Example 37a) in dry DMF (10 ml) was cooled in an ice-bath and sodium hydride (60% dispersion in oil) (0.15 g, 3.7 mmol) added with stirring. The ice bath was removed and the reaction stirred for three quarters of a hour. A solution of the benzyl chloride (Example 37b) (as its free base) (0.77 g, 3.35 mmol) in DMF (5 ml) was added rapidly and the reaction stirred at room temperature for 3 hours.

The solvent was removed in vacuo, water added and extracted with ethyl acetate. The combined organic extracts were washed with brine, dried, filtered and evaporated in vacuo. The product was purified by flash chromatography on silica, eluting with 35% ethyl acetate in hexane to yield colourless crystals.

ii) 5-<1-{3-[2(E)-(2-Pyridyl)ethenyl]benzyl}indol-7-yl ethyl>1H-tetrazole

The nitrile (Example 37c part i) (0.124 g, 0.34 mmol) and tributyl tin azide (0.169 g, 0.51 mmol) were heated at 150° C. under nitrogen for 1 hour. On cooling, the gum was taken up in dimethoxyethane (1 ml), acidified with acetic acid and allowed to crystallise at 0° C. The product was filtered off, washed with cold dimethoxyethane and dried in vacuo to yield a yellow-brown solid, m.p. 237°–239° C.

1H-NMR (300 MHz, DMSO-d6) $\delta$3.09 (2H, t), 3.23 (2H, t), 5.68 (2H, s), 6.58 (1H, d), 6.72 (1H, d), 6.82 (1H, dd), 6.94 (1H, t), 7.17–7.30 (4H), 7.46–7.55 (5H), 7.78 (1H, dt), 8.55 (1H, m).

EXAMPLE 38

5-<1-{3-[2(E)-(4-Isopropylthiazol-2-yl)ethenyl]benzyl}-indol-7-yl ethyl>-1H-tetrazole a) 3-[2(E)-(4-Isopropylthiazol-2-yl)ethenyl]benzyl chloride i) 3-[2(E)-(4-Isopropylthiazol-2-yl)ethenyl]benzaldehyde To a solution of diethyl 4-isopropylthiazol-2-ylmethyl phosphonate (3.8 g, 13.7 mmol) in dry THF (75 ml), cooled to −70° C. under nitrogen was added rapidly 2.5M n-butyl lithium (5.76 ml) in hexane, allowing the temperature to rise to ca. −40° C. during the addition. The cloudy mixture was stirred at −70° C. for 20 minutes, then added dropwise to a solution of isophthalaldehyde (2.75 g, 20.6 mmol) in dry THF (50 ml) cooled to −30° C. After addition was complete, the reaction mixture was allowed to warm to room temperature and stirred for a further 18 hours. The solvent was removed in vacuo, water added and extracted with diethyl ether. The combined organic extracts were washed with water, then brine, dried, filtered and evaporated in vacuo to a yellow oil.

ii) 3-[2(E)-(4-Isopropylthiazol-2-yl)ethenyl]benzyl alcohol

The crude aldehyde (Example 38a part i) was dissolved in ethanol (30 ml) and cooled in an ice bath. Sodium borohydride (1.73 g) was added portionwise, the ice bath removed and the reaction stirred for 40 minutes. Excess borohydride was destroyed and the solvent removed in vacuo. Diethyl ether was added to the residue and washed with water, then brine. The organic extract was dried, filtered and evaporated in vacuo. Purification by flash chromatography on silica, eluting with 40–60% diethyl ether in 60°–80° C. petrol yielded the product.

iii) 3-[2(E)-(4-Isopropylthiazol-2-yl)ethenyl]benzyl chloride

The benzyl alcohol (Example 38a part ii) was reacted with thionyl chloride as described in Example 38b part iv to yield the corresponding benzyl chloride as its hydrochloride salt.

b) 5-<1-{3-[2(E)-(4-Isopropylthiazol-2-yl)ethenyl]benzyl}-indol-7-yl ethyl>-1H-tetrazole The benzyl chloride (Example 38a) was reacted with 7-(2-cyanoethyl) indole (Example 37a) and converted to the tetrazole as described in Example 37c, m.p. 161°–163° C.

1H-NMR (300 MHz, DMSO-d6) $\delta$1.26 (6H, d), 3.05 (1H, m), 3.08 (2H, t), 3.26 (2H, t), 5.67 (2H, s), 6.58 (1H, d), 6.72 (1H, d), 6.81 (1H, d), 6.94 (1H, t), 7.24–7.36 (5H), 7.48 (1H, dd), 7.50 (1H, d), 7.56 (1H, d). MS [M+H]=455.

EXAMPLE 39

5-<1-{3-[2(E)-(4-Cyclopropylthiazol-2-yl)ethenyl]benzyl}-indol-7-yl ethyl>-1H-tetrazole This compound was synthesised according to the methods described for Example 38, m.p. 204°–207° C.

1H-NMR (300 MHz, DMSO-d6) $\delta$0.82–0.91 (4H, m), 2.08 (1H, m), 3.07 (2H, t), 3.25 (2H, t), 5.66 (2H, s), 6.57 (1H, d), 6.70 (1H, d), 6.80 (1H, dd), 6.93 (1H, t), 7.46–7.55 (4H), 7.23–7.30 (4H).

EXAMPLE 40

5-<1-[α-Phenyl-3-{2(E)-(quinolin-2-yl)ethenyl}benzyl]indol-6-yl methyl>-1H-tetrazole i) 1-[α-Phenyl-3-{2(E)-(quinolin-2-yl)ethenyl}benzyl]indole-6-carboxaldehyde Powdered potassium hydroxide (0.50 g, 8.93 mmol) was added to a stirred solution of indole-6-carboxaldehyde (Example 29a) (0.54 g, 3.70 mmol) in dimethyl-sulphoxide (10 ml). The solution was stirred under nitrogen for 10 minutes then solid a-phenyl-3-[2(E)-(quinolin-2-yl)ethenyl]benzyl chloride hydrochloride (Example 16a) (1.75 g, 4.46 mmol) was added and then stirred mixture was heated at 60° C. for 4 hours. The mixture was poured onto ammonium chloride solution and extracted with dichloromethane and the extract was dried and evaporated. The residue was chromatographed on silica in ethyl acetatehexane (1:3) to give a gummy solid which was recrystallised from ether-hexane, m.p. 75° C.

ii) 1-[α-Phenyl-3-{2(E)-(quinolin-2-yl)ethenyl}benzyl]indole-6-methanol

Solid sodium borohydride (0.11 g, 2.89 mmol) was added to a stirred suspension of 1-[α-phenyl-3-{2(E)-(quinolin-2-yl)ethenyl}benzyl]indole-6-carboxaldehyde (0.32 g, 0.69 mmol) in methanol (10 ml) and the mixture was stirred for 30 minutes giving a clear solution which was poured onto ammonium chloride solution and extracted with dichloromethane. The extract was dried and evaporated to give a solid product.

iii)
6-Chloromethyl-1-[α-phenyl-3-{2(E)-(quinolin-2-yl)ethenyl}benzyl]indole N-Chlorosuccinimide (0.11 g, 0.85 mmol) was added to a stirred solution of 1-[α-phenyl-3-{2(E)-(quinolin-2-yl)ethenyl}benzyl]indole-6-methanol (0.33 g, 0.71 mmol) and triphenyl phosphine (0.22 g, 0.85 mmol) in dichloromethane (5 ml). The solution was stirred for 2 hours, then chromatographed on silica eluting with ethyl acetate-hexane (1:3) to give a pale gum.

iv)
1-[α-Phenyl-3-{2(E)-(quinolin-2-yl)ethenyl}benzyl]-indole-6-acetonitrile A solution of 6-chloromethyl-1-[α-phenyl-3-{2(E)-(quinolin-2-yl)ethenyl}benzyl]indole (0.21 g, 0.43 mmol) and potassium cyanide (42 mg, 0.65 mmol) in dimethylsulphoxide (5 ml) was stirred for 3 hours, poured onto ammonium chloride solution and extracted with dichloromethane. The extract was dried and evaporated and the residue was chromatographed on silica in ethyl acetate-hexane (1:3) to give a pale gum.

v)
5-<1-[α-Phenyl-3-{2(E)-(quinolin-2-yl)ethenyl}benzyl]indol-6-yl methyl>-1H-tetrazole This compound was prepared by the method described in Example 14c part ii. The dimethoxy ethane solution was acidified with acetic acid, concentrated to low volume and diluted with ether to give a yellow solid m.p. 182° C.

NMR (300 MHz, (CD$_3$)$_2$SO) δ4.32 (2p, s, CH$_2$ Tet), 6.51 (1p, indole 3H), 7.42, 7.80 (two 1p, d, —CH=CH—).

EXAMPLES 41 AND 42

Geometric isomers of
5-<2-[1-{3-(2E)-(7-chloroquinolin-2-yl)ethenyl)benzyl}indol-7-yl]ethenyl>-1H-tetrazole Tetrazol-5-ylmethyl triphenyl phosphinium betaine (0.38 g, 1.1 mmol) in dry THF (10 ml) was cooled in an ice bath under nitrogen and 1.5M lithium diisopropylamide in THF (0.8 ml, 1.2 mmol) added with stirring. The mixture was stirred at 0° C. for half an hour, then 1-{3-[2(E)-(7-chloroquinolin-2-yl)ethenyl]benzyl}indol-7-yl-carboxaldehyde (prepared as for Example 13a) (0.43 g, 1 mmol) in dry THF (5 ml) was added in one portion. The mixture was stirred overnight at room temperature. Methanol (25 ml) was added and the crude reaction mixture preadsorbed onto silica before separation by flash chromatography on silica, eluting first with 50% acetone in hexane to yield 0.20 g of unreacted aldehyde, then with 10% methanol in dichloromethane to yield a crude sample of the two geometric isomers of the product. The crude product was suspended in chloroform (5 ml), sonicated and the solid removed by filtration to give 5-<2(E)-[1-{3-(2(E)-(7-chloroquinolin-2-yl)ethenyl)benzyl}indol-7-yl]ethenyl>-1H-tetrazole.

$^1$H-NMR (300 MHz, DMSO-d$^6$) δ6.65 (1H, d, indole-3H), 6.89/8.29 (2×1H, d, CH=CH Tet), 7.30 (1H, d, CH=CH-quinoline), 7.64 (1H, d, CH=CH-quinoline), 7.64 (1H, d, indole-2H).

The mother liquors were purified by preparative RP-HPLC on a Dynamax C18 column, eluting with 85:15:0.2 methanol/water/acetic acid, to yield further trans product and 5-<2(Z)-[1-{3-(2(E)-(7-chloroquinolin-2-yl)ethenyl)benzyl}indol-7-yl]ethenyl>-1H-tetrazole.

$^1$H-NMR (300 MHz, DMSO-d$^6$) δ6.62 (1H, d, indole-3H), 5.5/5.7 (2×1H, d, CH=CH Tet), 7.36 (1H, d, CH=CH-quinoline), 7.51 (1H, d, indole-2H), 7.75 (1H, d, CH=CH-quinoline).

EXAMPLE 43

5-<2-{1-[3-(2-(7-Chloroquinolin-2-yl)ethyl)benzyl]indol-7-yl}-ethyl>-1H-tetrazole 5-<2-{1-[3-(2-(7-Chloroquinolin-2-yl)ethenyl)benzyl]indol-7-yl}ethyl>-1H-tetrazole (Example 14) (0.3 g, 0.61 mmol) was suspended in methanol (100 ml) and 0.2M sodium hydroxide (3.35 ml, 0.67 mmol) added. 10% Palladium on carbon (0.1 g) was added to the resultant solution and the reaction mixture hydrogenated in a Parr apparatus at 65 p.s.i. for 10 hours. The catalyst was filtered off by passage through Celite, the filtrate acidified with acetic acid and the solvent removed in vacuo.

Purification by RP-HPLC on a C18 column, eluting with methanol/water/acetic acid (78:22:0.1) yielded required product with a faster eluting contaminant. Recrystallisation from ethyl acetate/diethyl ether gave 5-<2-{1-[3-(2-(7-chloroquinolin-2-yl)ethyl)benzyl]indol-7-yl}ethyl>-1H-tetrazole, m.p. 163°–5° C.

$^1$H-NMR (300 MHz, DMSO-d$^6$) δ2.93–3.18 (8H, m, 4×CH$_2$), 5.60 (2H, S, NCH$_2$), 6.50 (1H, d, indole-3H), 7.38 (1H, d, indole-2H). MS [M+H]=493.

EXAMPLE 44

The following compounds are made by similar methods to those described in the above Examples.

5-<2-{1-[3-(2-Benzthiazol-2-ylethenyl)benzyl]indol-7-yl}ethyl>-1H-tetrazole.
5-<2-{1-[3-(2-Benzoxazol-2-ylethenyl)benzyl]indol-7-yl}-ethyl>-1H-tetrazole.
5-<2-{1-[3-(2-Quinoxalin-2-ylethenyl)benzyl]indol-7-yl}-ethyl>-1H-tetrazole.
5-<2-{1-[3-(2-Quinazolin-2-ylethenyl)benzyl]indol-7-yl}-ethyl>-1H-tetrazole.

The following formulations illustrate the invention.

EXAMPLE 45

Soft Gelatin Capsule

Each soft gelatin capsule contains:

| Active ingredient | 150 mg |
|---|---|
| Arachis oil | 150 mg |

After mixing together, the blend is filled into soft gelatine capsules using the appropriate equipment.

EXAMPLE 46

Hard Gelatine Capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 47

Aerosol

| Active ingredient | 10 mg |
|---|---|
| Ethanol | 50 mg |
| Dichlorodifluoromethane (Propellant 12) | 658 mg |
| Dichlorotetrafluoroethane (Propellant 114) | 282 mg |

The active ingredient is dissolved in the ethanol. The concentrate is filled into extruded aluminum cans for inhalation aerosols. The cans are degassed with propellant 12 and sealed with an appropriate metered dose valve. The volume of product expelled per actuation is 50 to 100 μl equivalent to 0.5–1 mg active ingredient.

We claim:

1. A compound of the formula

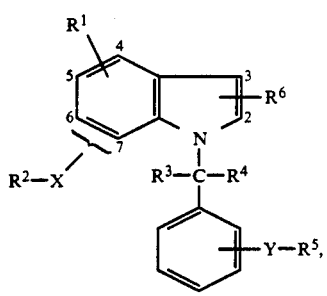

in which $R^1$ is hydrogen, halo, $C_{1-4}$ alkyl, $C_{1-4}$ alkoxy, nitrile, optionally protected carboxy, optionally protected tetrazolyl, trihalomethyl, hydroxy-$C_{1-4}$ alkyl, aldehydo, —$CH_2Z$, —$CH=CH—Z$ or —$CH_2CH_2Z$ where Z is optionally protected carboxy or optionally protected tetrazolyl; $R^2$ is halo, nitrile, an optionally protected acid group or —$CONR^7R^8$ where $R^7$ and $R^8$ are each hydrogen or $C_{1-4}$ alkyl; $R^3$ and $R^4$ are each hydrogen, $C_{1-4}$ alkyl, optionally substituted phenyl, or $C_{1-4}$ alkyl substituted by —$CONR^7R^8$ or an optionally protected acid group; $R^5$ is

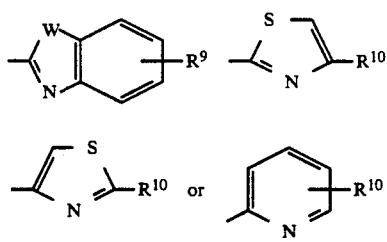

where W is —CH=CH—, —CH=N—, —N=CH—, —O— or —S—, $R^9$ is hydrogen, halo, $C_{1-4}$ alkyl, $C_{1-4}$ alkoxy or trihalomethyl, and $R^{10}$ is hydrogen, $C_{1-4}$ alkyl, $C_{2-6}$ alkenyl, $C_{3-6}$ cycloalkyl or $C_{1-4}$ alkyl-$C_{3-6}$ cycloalkyl; $R^6$ is hydrogen or $C_{1-4}$ alkyl; X is —O—$(CH_2)_nCR^{11}R^{12}$, —$CR^{11}R^{12}$—, —$CR^{11}R^{12}.(CH_2)_n.CR^{13}R^{14}$— or —$CR^{11}=CR^{12}$— where $R^{11}$, $R^{12}$, $R^{13}$ and $R^{14}$ are each hydrogen or $C_{1-4}$ alkyl, and n is 0, 1 or 2; and Y is —O—$CR^{15}R^{16}$—, —$CR^{15}=CR^{16}$— or —$CR^{15}R^{16}.CR^{17}R^{18}$— where $R^{15}$, $R^{16}$, $R^{17}$ and $R^{18}$ are each hydrogen or $C_{1-4}$ alkyl; or a salt thereof.

2. A compound according to claim 1 in which $R^1$ is hydrogen or halo, $R^2$ is an acid group, $R^{11}$ to $R^{18}$ are hydrogen, and n is 0.

3. A compound according to claim 2 in which (i) $R^3$ and $R^4$ are both hydrogen, (ii) $R^3$ is hydrogen and $R^4$ is $C_{1-4}$ alkyl or optionally substituted phenyl, (iii) $R^3$ and $R^4$ are each $C_{1-4}$ alkyl or (iv) $R^3$ is $C_{1-4}$ alkyl substituted by an acid group and $R^4$ is hydrogen or $C_{1-4}$ alkyl.

4. A compound according to claim 3 in which $R^5$ is quinolin-2-yl and $R^9$ is hydrogen or halo.

5. A compound of the formula

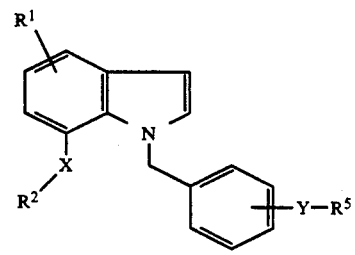

in which $R^1$ is hydrogen, halo, $C_{1-4}$ alkyl, $C_{1-4}$ alkoxy, nitrile, carboxy, $C_{1-4}$ alkoxy-carbonyl or trihalomethyl; $R^2$ is tetrazolyl, nitrile, carboxy, $C_{1-4}$ alkoxy-carbonyl or —$CONR^7R^8$ where $R^7$ and $R^8$ are each hydrogen or $C_{1-4}$ alkyl; $R^5$ is

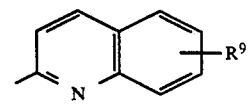

where $R^9$ is hydrogen, halo, $C_{1-4}$ alkyl, $C_{1-4}$ alkoxy or trihalomethyl; X is —O—$CR^{11}R^{12}$—, —$CR^{11}R^{12}.CR^{13}R^{14}$— or —$CR^{11}=CR^{12}$— where $R^{11}$, $R^{12}$, $R^{13}$ and $R^{14}$ are each hydrogen or $C_{1-4}$ alkyl; and Y is —O—$CR^{15}R^{16}$— or —$CR^{15}=CR^{16}$— where $R^{15}$ and $R^{16}$ are each each hydrogen or $C_{1-4}$ alkyl; or a salt thereof.

6. A compound of the formula

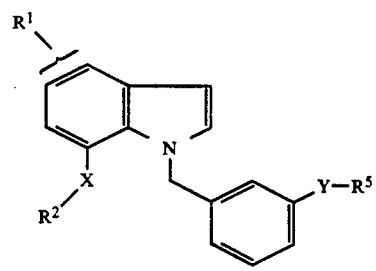

in which $R^1$ is hydrogen or halo, $R^2X$— is tetrazolyl—$CH_2O$— or tetrazolyl—$CH_2CH_2$—, and $R^5Y$— is

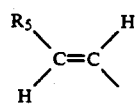

where $R^5$ is

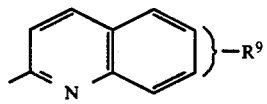

and R⁹ is hydrogen or halo; or a salt thereof.

7. A compound of the formula

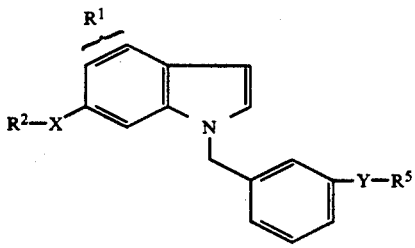

in which R¹ is hydrogen or halo, R²X— is tetrazolyl—CH₂—, and R⁵Y— is

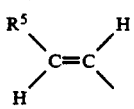

where R⁵ is

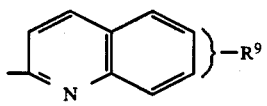

and R⁹ is hydrogen or halo; or a salt thereof.

8. 5-<2-[1-{3-(2(E)-(7-Chloroquinolin-2-yl)ethenyl)-benzyl}indol-7-yl]ethyl>-1H-tetrazole or a pharmaceutically-acceptable salt thereof.

9. A pharmaceutical formulation comprising a compound according to claim 1, in unprotected form, or a pharmaceutically-acceptable salt thereof, together with a pharmaceutically-acceptable diluent or carrier therefor.

10. A method of treating an animal, including a human, suffering from or susceptible to a disease in which leukotrienes are a causal mediator which comprises administering an effective amount of a compound according to claim 1, in unprotected form, or a pharmaceutically-acceptable salt thereof.

11. A compound according to claim 1 which is 5-<1-[3-{2(E)-(Quinolin-2-yl)ethenyl}benzyl]indol-7-yloxymethyl>-1H-tetrazole or a pharmacologically acceptable salt thereof.

12. A compound according to claim 1 which is 5-<5-Carboxy-1-[3-{2(E)-(quinolin-2-yl)ethenyl}benzyl]indol-7-yloxymethyl>-1H-tetrazole or a pharmacologically acceptable salt thereof.

13. A compound according to claim 1 which is 5-<4-Chloro-1-[3-{2(E)-(quinolin-2-yl)ethenyl}benzyl]indol-7-yloxymethyl>-1H-tetrazole or a pharmacologically acceptable salt thereof.

14. A compound according to claim 1 which is 5-<4-Carboxy-1-{3-[2-(E)-(quinolin-2-yl)ethenyl]benzyl}indol-7-yloxymethyl>-1H-tetrazole or a pharmacologically acceptable salt thereof.

15. A compound according to claim 1 which is 5-<1-[3-(Quinolin-2-ylmethoxy)benzyl]indol-7-yloxymethyl>-1H-tetrazole or a pharmacologically acceptable salt thereof.

16. A compound according to claim 1 which is 5-<1-{3-[2(E)-(7-Chloroquinolin-2-yl)ethenyl]benzyl}indol-7-yloxymethyl>-1H-tetrazole or a pharmacologically acceptable salt thereof.

17. A compound according to claim 1 which is 5-<4-Chloro-1-{3-[2(E)-(7-chloroquinolin-2-yl)ethenyl]benzyl}indol-7-yloxymethyl>-1H-tetrazole or a pharmacologically acceptable salt thereof.

18. A compound according to claim 1 which is 5-<1-[3-(7-Chloroquinolin-2-ylmethoxy)benzyl]indol-7-yloxy-methyl>-1H-tetrazole or a pharmacologically acceptable salt thereof.

19. A compound according to claim 1 which is 5-<2-[1-{3-(2-(E)-(Quinolin-2-yl)ethenyl)benzyl}indol-7-yl]ethyl>-1H-tetrazole or a pharmacologically acceptable salt thereof.

20. A compound according to claim 1 which is 5-<4-Trifluoromethyl-1-[3-{2(E)-(7-chloroquinolin-2-yl)ethenyl}benzyl]indol-7-yloxymethyl>-1H-tetrazole or a pharmacologically acceptable salt thereof.

21. A compound according to claim 1 which is 1-[3-{2(E)-(7-Chloroquinolin-2-yl)ethenyl}benzyl]indol-7-yl-oxyacetic acid or a pharmacologically acceptable salt thereof.

22. A compound according to claim 1 which is 5-<1-{3-[2(E)-(Quinolin-2-yl)ethenyl]benzyl}indol-7-ylmethyl>-1H-tetrazole or a pharmacologically acceptable salt thereof.

23. A compound according to claim 1 which is 5-<2-[1-{3-(2(E)-(7-Chloroquinolin-2-yl)ethenyl)benzyl}indol-7-yl]ethyl>-1H-tetrazole or a pharmacologically acceptable salt thereof.

24. A compound according to claim 1 which is 5-<3-[1-{3-(2(E)-(7-Chloroquinolin-2-yl)ethenyl)benzyl}indol-7-yl]propyl>-1H-tetrazole or a pharmacologically acceptable salt thereof.

25. A compound according to claim 1 which is 5-<1-[α-Phenyl-3-{2-(E)-(quinolin-2-yl)ethenyl}benzyl]indol-7-yloxymethyl>-1H-tetrazole; represented by the formula:

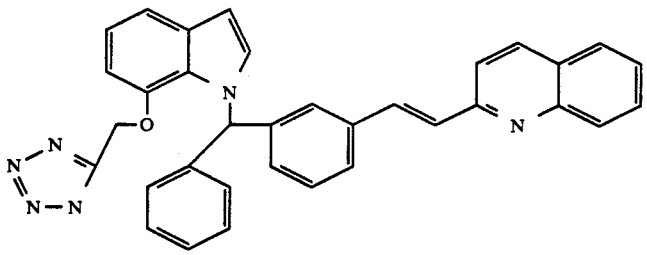

or a pharmacologically acceptable salt thereof.

26. A compound according to claim 1 which is 5-<2-[1-{4-(2(E)-(7-Chloroquinolin-2-yl)ethenyl)benzyl}indol-7-yl]ethyl>-1H-tetrazole or a pharmacologically acceptable salt thereof.

27. A compound according to claim 1 which is 5-<4-(2-Carboxyethyl)-1-[3-{2(E)-(quinolin-2-yl)ethenyl}benzyl]-indol-7-yloxymethyl>-1H-tetrazole or a pharmacologically acceptable salt thereof.

28. A compound according to claim 1 which is 5-<1-[α-{3-(1H-Tetrazol-5-yl)phenyl}-3-{2(E)-(quinolin-2-yl)ethenyl}benzyl]indol-7-yloxymethyl>-1H-tetrazole; represented by the formula:

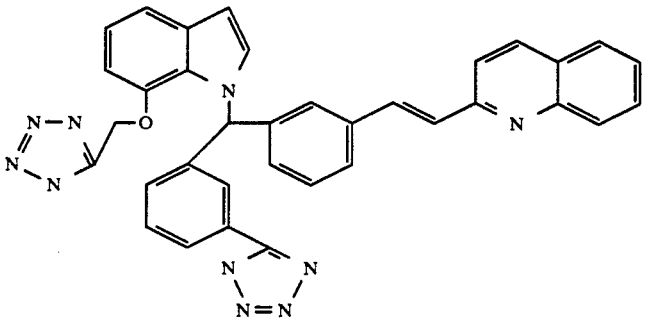

or a pharmacologically acceptable salt thereof.

29. A compound according to claim 1 which is 5-<1-{3-[2(E)-(7-Chloroquinolin-2-yl)ethenyl]-α-phenyl-benzyl}indol-7-yloxymethyl>-1H-tetrazole or a pharmacologically acceptable salt thereof.

30. A compound according to claim 1 which is 5-<1-{α-(3-Chlorophenyl)-3-[2(E)-(7-chloroquinolin-2-yl)ethenyl]benzyl}indol-7-yloxymethyl>-1H-tetrazole or a pharmacologically acceptable salt thereof.

31. A compound according to claim 1 which is 5-<1-{α-(4-Chlorophenyl)-3-[2(E)-(7-chloroquinolin-2-yl)ethenyl]benzyl}indol-7-yloxymethyl>-1H-tetrazole or a pharmacologically acceptable salt thereof.

32. A compound according to claim 1 which is 5-<1-{3-[2(E)-(7-Chloroquinolin-2-yl)ethenyl]-α-(3-methoxyphenyl)benzyl}indol-7-yloxymethyl>1H-tetrazole or a pharmacologically acceptable salt thereof.

33. A compound according to claim 1 which is 5-<1-{3-[2(E)-(7-Chloroquinolin-2-yl)ethenyl]-α-(4-methylphenyl)benzyl}indol-7-yloxymethyl>-1H-tetrazole or a pharmacologically acceptable salt thereof.

34. A compound according to claim 1 which is 5-<1-[α-{4-(1H-Tetrazol-5-yl)phenyl}-3-{2(E)-(quinolin-2-yl)ethenyl}benzyl]indol-7-yloxymethyl>-1H-tetrazole; represented by the formula:

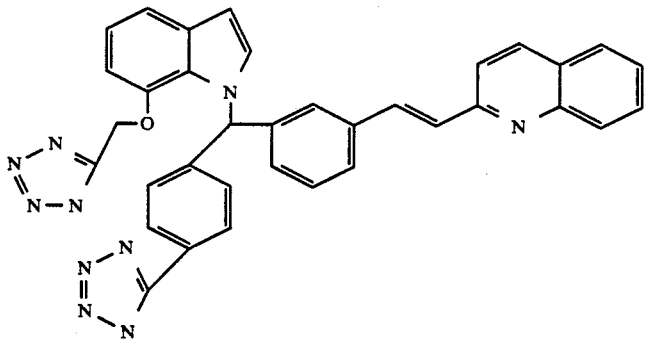

or a pharmacologically acceptable salt thereof.

35. A compound according to claim 1 which is 3-{1-<3-[2(E)-(7-Chloroquinolin-2-yl)ethenyl]benzyl>indol-7-yl}propanoic acid or a pharmacologically acceptable salt thereof.

36. A compound according to claim 1 which is 5-<1-{3-[2(E)-(7-Chloroquinolin-2-yl)ethenyl]benzyl}-indol-6-yl methyl>-1H-tetrazole or a pharmacologically acceptable salt thereof.

37. A compound according to claim 1 which is 5-<2-[1-{3-[2(E)-(7-Chloroquinolin-2-yl)ethenyl]benzyl}indol-6-yl ethyl>-1H-tetrazole or a pharmacologically acceptable salt thereof.

38. A compound according to claim 1 which is 5-<1-[1-{3-[2(E)-(7-Chloroquinolin-2-yl)ethenyl benzyl}indol-6-yl]ethyl>-1H-tetrazole or a pharmacologically acceptable salt thereof.

39. A compound according to claim 1 which is 5-<2-{1-[3-{2(E)-(7-Chloroquinolin-2-yl)ethenyl}benzyl]-indol-7-yl}-1-methyl ethyl>-1H-tetrazole or a pharmacologically acceptable salt thereof.

40. A compound according to claim 1 which is 5-<1-{3-[2(E)-(7-Chloroquinolin-2-yl)ethenyl]benzyl}-3-methyl-indol-7-yl ethyl>1H-tetrazole or a pharmacologically acceptable salt thereof.

41. A compound according to claim 1 which is 5-<1-{3-[2(E)-(7-Chloroquinolin-2-yl)ethenyl]-α-methyl-benzyl}indol-7-yl oxymethyl>-1H-tetrazole; represented by the formula:

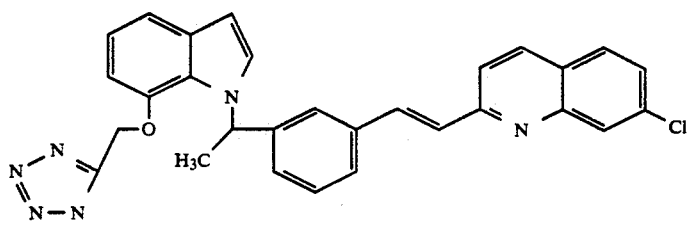

or a pharmacologically acceptable salt thereof.

42. A compound according to claim 1 which is 5-<1-{3-[2(E)-(2-Pyridyl)ethenyl]benzyl}indol-7-yl ethyl>-1H-tetrazole or a pharmacologically acceptable salt thereof.

43. A compound according to claim 1 which is 5-<1-{3-[2(E)-(4-Isopropylthiazol-2-yl)ethenyl]benzyl}-indol-7-yl ethyl>-1H-tetrazole or a pharmacologically acceptable salt thereof.

44. A compound according to claim 1 which is 5-<1-{3-[2(E)-(4-Cyclopropylthiazol-2-yl)ethenyl]benzyl}-indol-7-yl ethyl>-1H-tetrazole or a pharmacologically acceptable salt thereof.

45. A compound according to claim 1 which is 5-<1-[α-Phenyl-3-{2(E)-(quinolin-2-yl)ethenyl}benzyl]indol-6-yl methyl>-1H-tetrazole or a pharmacologically acceptable salt thereof.

46. A compound according to claim 1 which is 5-<2-[1-{3-(2E)-(7-chloroquinolin-2-yl)ethenyl)benzyl}indol-7-yl]ethenyl>-1H-tetrazole or a pharmacologically acceptable salt thereof.

47. A compound according to claim 1 which is 5-<2-{1-[3-(2-Benzthiazol-2-ylethenyl)benzyl]indol-7-yl}-ethyl>-1H-tetrazole or a pharmacologically acceptable salt thereof.

48. A compound according to claim 1 which is 5-<2-{1-[3-(2-Benzoxazol-2-ylethenyl)benzyl]indol-7-yl}-ethyl>-1H-tetrazole or a pharmacologically acceptable salt thereof.

49. A compound according to claim 1 which is 5-<2-{1-[3-(2-Quinoxalin-2-ylethenyl)benzyl]indol-7-yl}-ethyl>-1H-tetrazole or a pharmacologically acceptable salt thereof.

50. 5-<1-{3-[2(E)-(7-Chloroquinolin-2-yl)ethenyl]-α-[3-(1H-tetrazol-5-yl)propyl]benzyl}indol-7-yl oxymethyl>-1H-tetrazole or a pharmacologically acceptable salt thereof.

51. 5-<1-[4-{2(E)-(Quinolin-2-yl)ethenyl}benzyl]indol-7-yloxymethyl>-1H-tetrazole or a pharmacologically acceptable salt thereof.

52. 5-<1-{3-[2(E)-(7-Chloroquinolin-2-yl)ethenyl]-α-(3-trifluoromethylphenyl)benzyl}indol-7-yloxymethyl>-1H-tetrazole or a pharmacologically acceptable salt thereof.

53. 5-<1-{3-[2(E)-(7-Chloroquinolin-2-yl)ethenyl]-α-ethyl-benzyl}indol-7-yloxymethyl>-1H-tetrazole or a pharmacologically acceptable salt thereof.

54. A pharmaceutical formulation comprising a compound according to claim 50, in unprotected form, or a pharmaceutically acceptable salt thereof, together with a pharmaceutically acceptable diluent or carrier therefor.

55. A pharmaceutical formulation comprising a compound according to claim 51, in unprotected form, or a pharmaceutically acceptable salt thereof, together with a pharmaceutically acceptable diluent or carrier therefor.

56. A pharmaceutical formulation comprising a compound according to claim 36, in unprotected form, or a pharmaceutically acceptable salt thereof, together with a pharmaceutically acceptable diluent or carrier therefor.

57. A pharmaceutical formulation comprising a compound according to claim 53, in unprotected form, or a pharmaceutically acceptable salt thereof, together with a pharmaceutically acceptable diluent or carrier therefor.

58. A method of treating an animal, including a human, suffering from or susceptible to a disease in which leukotrienes are a causal mediator which comprises administering an effective amount of a compound according to claim 50, in unprotected form, or a pharmaceutically acceptable salt thereof.

59. A method of treating an animal, including a human, suffering from or susceptible to a disease in which leukotrienes are a causal mediator which comprises administering an effective amount of a compound according to claim 51, in unprotected form, or a pharmaceutically acceptable salt thereof.

60. A method of treating an animal, including a human, suffering from or susceptible to a disease in which leukotrienes are a causal mediator which comprises administering an effective amount of a compound according to claim 36, in unprotected form, or a pharmaceutically acceptable salt thereof.

61. A method of treating an animal, including a human, suffering from or susceptible to a disease in which leukotrienes are a causal mediator which comprises administering an effective amount of a compound according to claim 53, in unprotected form, or a pharmaceutically acceptable salt thereof.

* * * * *

UNITED STATES PATENT AND TRADEMARK OFFICE
CERTIFICATE OF CORRECTION

PATENT NO. : 5,281,593
DATED : January 25, 1994
INVENTOR(S) : Jeremy Gilmore, et al It is certified that error appears in the above-indentified patent and that said Letters Patent is hereby corrected as shown below:

Column 3, line 6, reads "...-O-$(CH_2)_n CR^{11}R^{12}$ via the oxygen atom..."; it should read -- ...-O-$(CH_2)_n.CR^{11}R^{12}$- via the oxygen atom... -- .

Column 42, line 48, reads "...(2-Pyridyl)ethye yl]benzyl chloride..."; it should read -- ...(2-Pyridyl)ethenyl]benzyl chloride... -- .

Column 53, line 57, reads "...ethyl>-1H-tetrazole..."; it should read -- ...ethyl>-1H-tetrazole... -- .

Column 53, line 61, reads "...ethyl>-1H-tetrazole..."; it should read -- ethyl>-1H-tetrazole... -- .

Column 53, line 65, reads "...ethyl>-1H-tetrazole..."; it should read -- ...ethyl>1H-tetrazole -- .

Signed and Sealed this

Eighteenth Day of October, 1994

Attest:

BRUCE LEHMAN

Attesting Officer     Commissioner of Patents and Trademarks